(12) United States Patent
Edwards et al.

(10) Patent No.: US 11,480,566 B2
(45) Date of Patent: Oct. 25, 2022

(54) WATER DISPERSIBLE ASSAYS

(71) Applicant: LIA Diagnostics, Inc., Philadelphia, PA (US)

(72) Inventors: Bethany Edwards, Philadelphia, PA (US); Anna Couturier, Philadelphia, PA (US); Kosha Kumar, Philadelphia, PA (US)

(73) Assignee: LIA Diagnostics, Inc., Philadelphia, PA (US)

( * ) Notice: Subject to any disclaimer, the term of this patent is extended or adjusted under 35 U.S.C. 154(b) by 878 days.

(21) Appl. No.: 15/749,223

(22) PCT Filed: Aug. 5, 2016

(86) PCT No.: PCT/US2016/045891
§ 371 (c)(1),
(2) Date: Jan. 31, 2018

(87) PCT Pub. No.: WO2017/024271
PCT Pub. Date: Feb. 9, 2017

(65) Prior Publication Data
US 2018/0224436 A1   Aug. 9, 2018

Related U.S. Application Data

(60) Provisional application No. 62/202,003, filed on Aug. 6, 2015, provisional application No. 62/208,217, filed
(Continued)

(51) Int. Cl.
*G01N 33/543* (2006.01)
*G01N 21/84* (2006.01)
(Continued)

(52) U.S. Cl.
CPC .......... *G01N 33/543* (2013.01); *B01L 3/5023* (2013.01); *G01N 21/78* (2013.01);
(Continued)

(58) Field of Classification Search
CPC .... G01N 33/543; G01N 21/78; G01N 33/549; G01N 33/558; G01N 33/559;
(Continued)

(56) References Cited

U.S. PATENT DOCUMENTS 5,246,664 A * 9/1993 Nagata ................. C09D 129/14
422/429
5,378,638 A * 1/1995 Deeg ................ G01N 33/54386
436/518

(Continued)

FOREIGN PATENT DOCUMENTS

| CN | 1208088 A | 2/1999 |
| CN | 1658902 A | 8/2005 |

(Continued)

OTHER PUBLICATIONS

Anonymous, "LIA—IPD: Integrated Product Design", Integrated Product Design Program, University of Pennsylvania, PA, USA, URL: https://ipd.me.upenn.edu/portfolio/lia/, retrieved on Nov. 15, 2018.
(Continued)

*Primary Examiner* — Christopher L Chin
(74) *Attorney, Agent, or Firm* — Rimon P.C.

(57) ABSTRACT

The present disclosure relates to water dispersible or soluble diagnostic assay methods, devices, kits, and methods of manufacture.

3 Claims, 19 Drawing Sheets

Related U.S. Application Data on Aug. 21, 2015, provisional application No. 62/362,813, filed on Jul. 15, 2016.

(51) Int. Cl.

| | | |
|---|---|---|
| *B01L 3/00* | (2006.01) | |
| *G01N 33/558* | (2006.01) | |
| *G01N 33/76* | (2006.01) | |
| *G01N 21/78* | (2006.01) | |
| *G01N 21/05* | (2006.01) | |
| *G01N 21/77* | (2006.01) | |

(52) U.S. Cl.
CPC ....... *G01N 21/8483* (2013.01); *G01N 33/558* (2013.01); *G01N 33/76* (2013.01); *B01L 2200/18* (2013.01); *B01L 2300/0819* (2013.01); *B01L 2300/0825* (2013.01); *B01L 2300/0887* (2013.01); *B01L 2300/126* (2013.01); *B01L 2300/165* (2013.01); *G01N 2021/058* (2013.01); *G01N 2021/7759* (2013.01)

(58) Field of Classification Search
CPC ............... G01N 33/76; G01N 21/8483; G01N 2021/058; G01N 2021/7759; B01L 3/5023; B01L 2300/0819; B01L 2200/18; B01L 2300/0887; B01L 2300/126; B01L 2300/165; B01L 2300/0825; B01L 2300/0848; B01L 2300/168
USPC ..... 422/401, 420, 425, 426; 435/287.9, 805, 435/970; 436/535, 810; 427/2.13, 466, 427/468

See application file for complete search history.

(56) References Cited

U.S. PATENT DOCUMENTS

| | | | |
|---|---|---|---|
| 5,509,913 A | 4/1996 | Yeo | |
| 5,552,288 A * | 9/1996 | Christensen | ......... G01N 33/558 435/7.9 |
| 6,403,298 B1 | 6/2002 | Lee et al. | |
| 6,808,598 B1 | 10/2004 | Takeuchi et al. | |
| 10,045,694 B2 * | 8/2018 | Edwards | ............... G01N 33/548 |
| 10,542,886 B2 * | 1/2020 | Edwards | ............... G01N 33/558 |
| 2005/0131362 A1 | 6/2005 | Przepasniak et al. | |
| 2008/0286879 A1 | 11/2008 | Lee | |
| 2008/0299005 A1 | 12/2008 | Meathrel et al. | |
| 2009/0054548 A1 | 2/2009 | Wang et al. | |
| 2009/0263854 A1 | 10/2009 | Jacono et al. | |
| 2009/0264836 A1 | 10/2009 | Roe et al. | |
| 2011/0105360 A1 * | 5/2011 | Derda | ................. G01N 33/548 506/10 |
| 2012/0072125 A1 | 3/2012 | Sharrock | |
| 2012/0130331 A1 | 5/2012 | Wang et al. | |
| 2013/0109837 A1 | 5/2013 | Bhandari et al. | |

FOREIGN PATENT DOCUMENTS

| | | |
|---|---|---|
| CN | 102099678 A | 6/2011 |
| CN | 102735835 A | 10/2012 |
| CN | 204241487 U | 4/2015 |
| EP | 801172 A1 | 10/1997 |
| JP | S6224145 A | 2/1987 |
| JP | H03162956 A | 7/1991 |
| JP | H0523716 B2 | 4/1993 |
| JP | H5149946 A | 6/1993 |
| JP | H0616043 B2 | 3/1994 |
| JP | H06201690 A | 7/1994 |
| JP | 2001115368 A | 4/2001 |
| JP | 2007513345 A | 5/2007 |
| JP | 2011183613 A1 | 9/2011 |
| WO | 9508761 A1 | 3/1995 |
| WO | 1997013920 A1 | 4/1997 |
| WO | 9808475 A1 | 3/1998 |
| WO | 2005054845 A1 | 6/2005 |
| WO | 2011018618 A2 | 2/2011 |
| WO | 2015175301 A1 | 11/2015 |
| WO | 2015181056 A1 | 12/2015 |

OTHER PUBLICATIONS

Emd Millipore, "Performance of Estapor Microspheres and Hi-Flow(TM) Plus Membranes in a Lateral Flow Assay for Human Chorionic Gonadotropin (hCG) EMD Millipore (Application Note)", URL: https://www.emdmillipore.com, retrieved on Nov. 16, 2018.
John Paul Titlow, "The Pregnancy Test Of The Future Is Flushable, Private, And Sustainable", Fast Company, URL: https://www.fastcompany.com/3047152/the-pregnancy-test-of-the-future-is-flushable-private-and-ustainable, retrieved on Nov. 16, 2018.
Wang et al., "Monitoring the Disease Activity via the Antibody-Antigen Recognition in Paper", Nano/Micro Engineered and Molecular Systems (NEMS), 2013 8th IEEE International Conference on (pp. 229-232). IEEE.
Zhihua Zhang et al, "Hydrophobic Silica Aerogels Strengthened with Nonwoven Fibers", Journal of Macromolecular Science, Part A—Pure and Applied Chemistry, Feb. 7, 2007, vol. 43, No. 11, pp. 1663-1670.
Fortea-Verdejo Marta et al, "Upgrading flax nonwovens: Nanocellulose as binder to produce rigid and robust flax fibre preforms", Composites Part A: Applied Science and Manufacturing, Nov. 17, 2015, vol. 83, pp. 63-71.

* cited by examiner

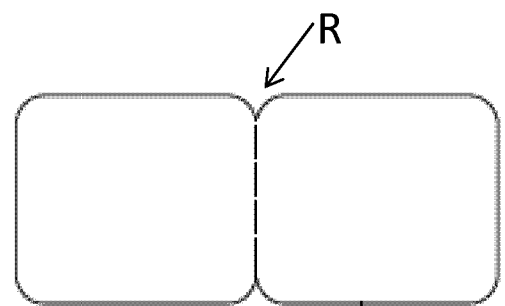
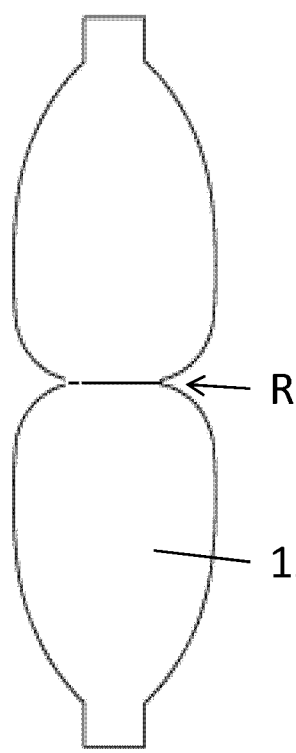
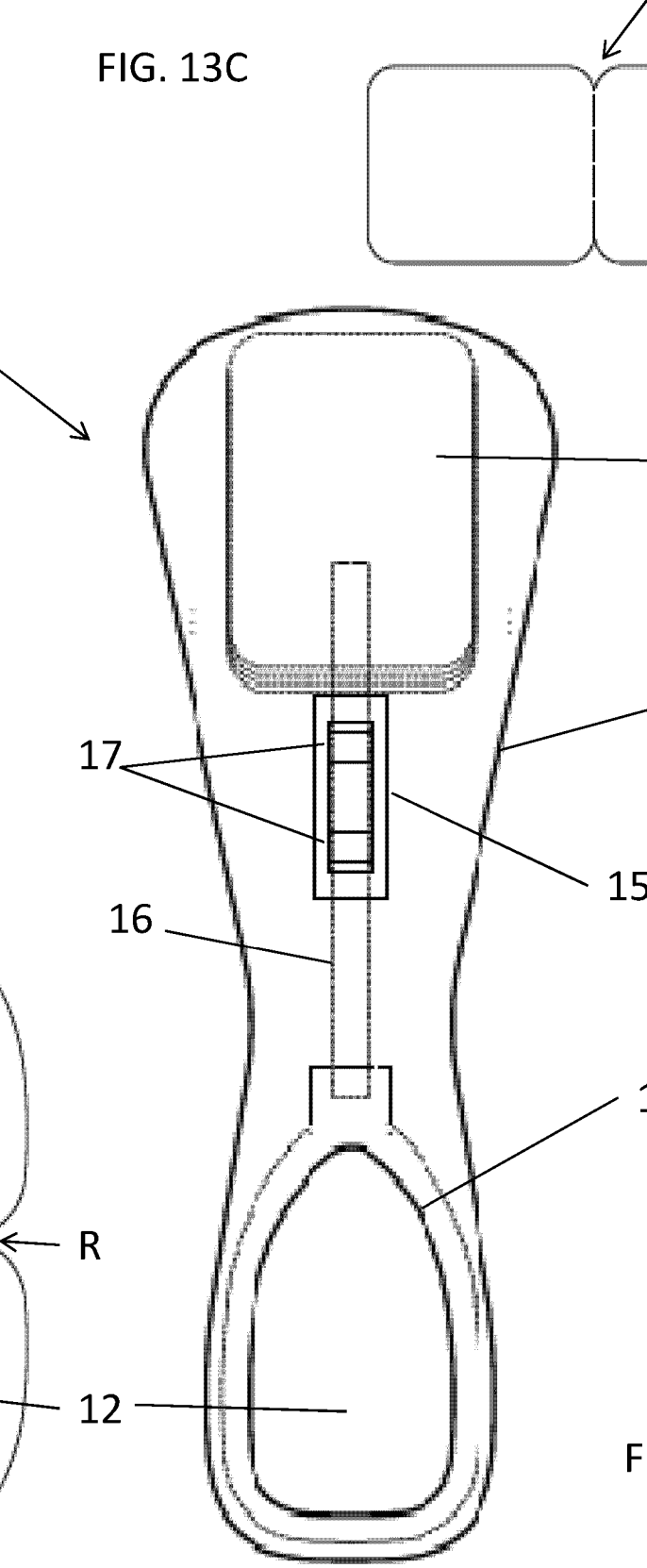

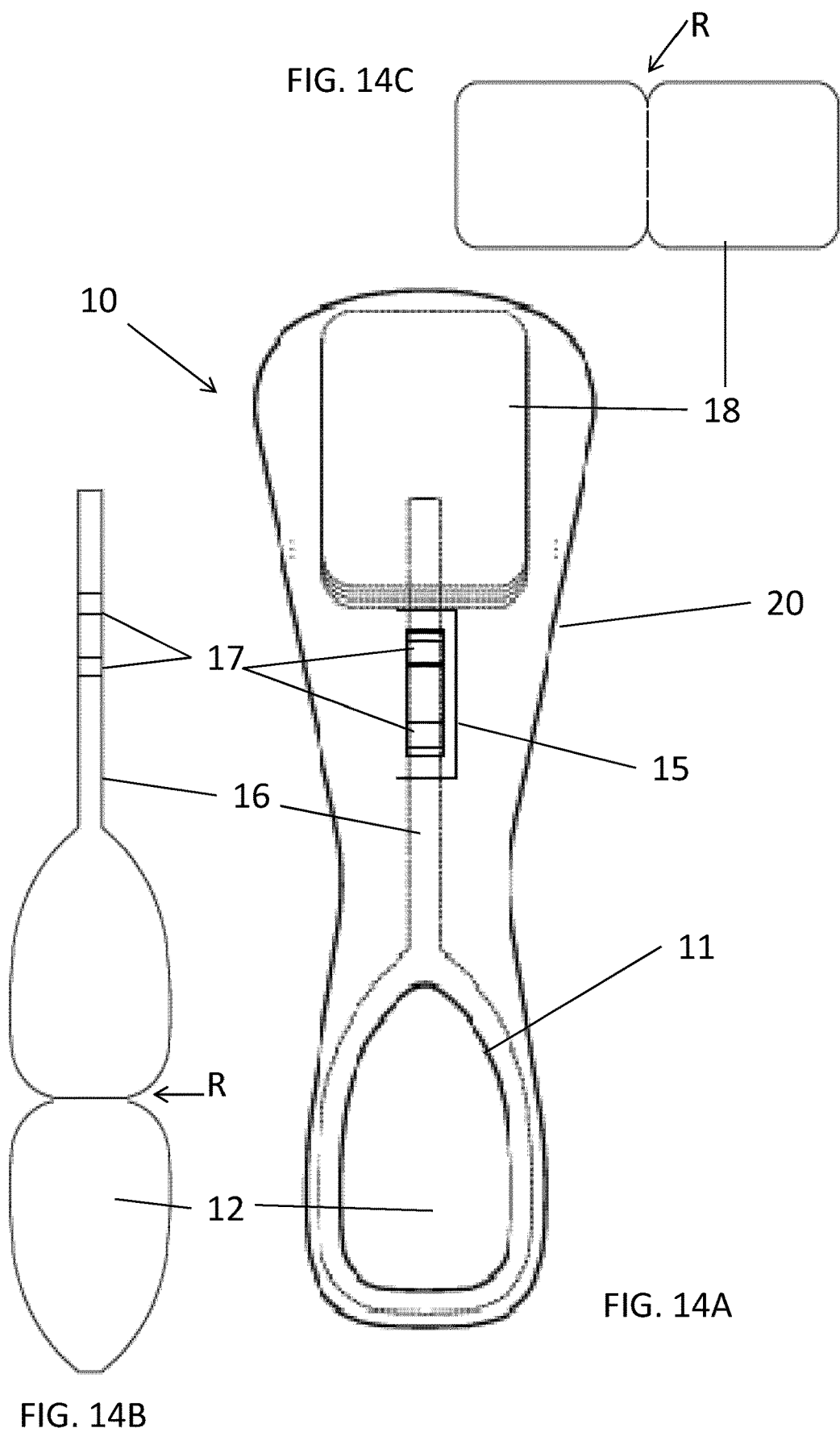

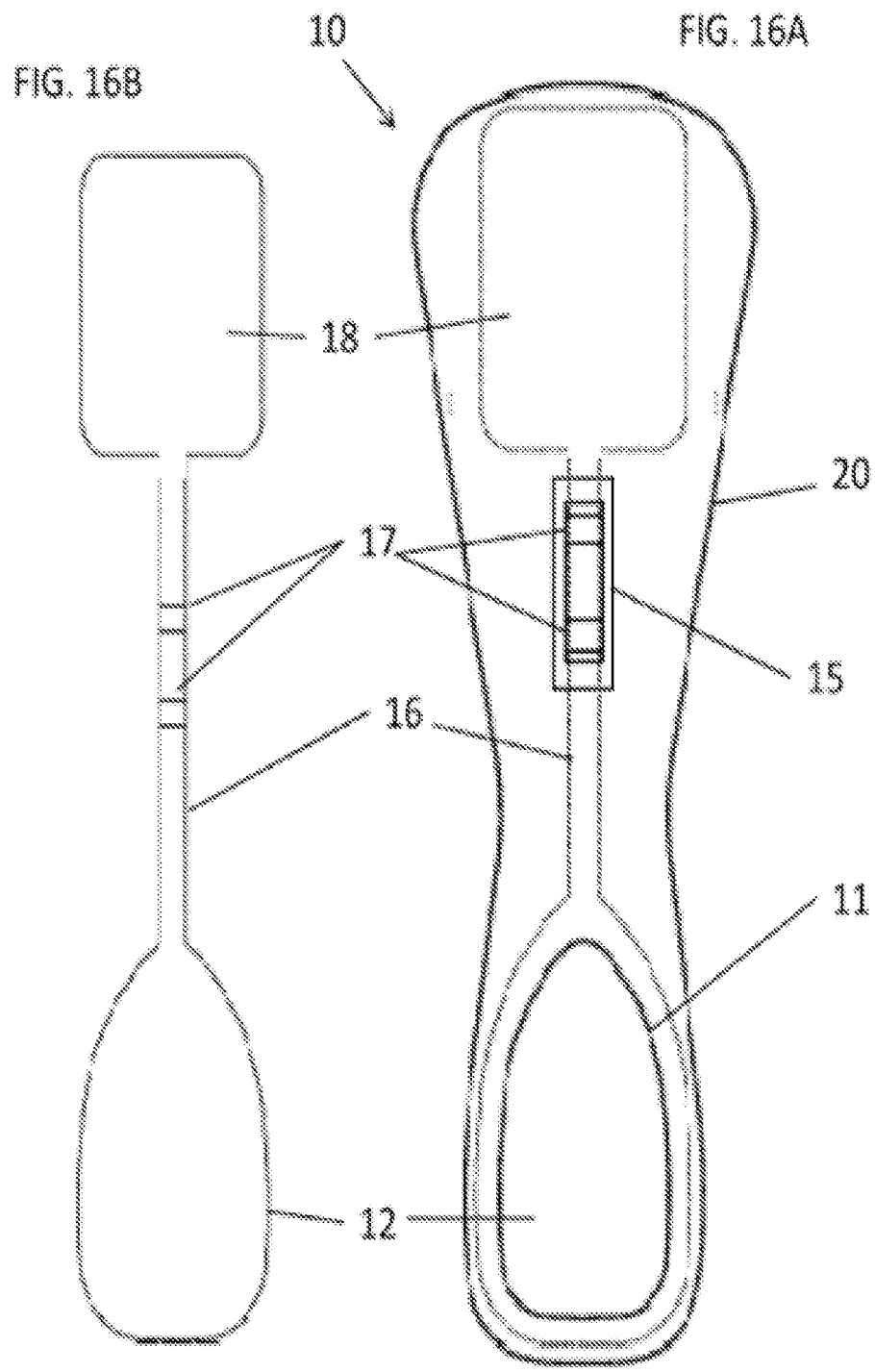

WATER DISPERSIBLE ASSAYS

CROSS-REFERENCE TO RELATED APPLICATIONS

This Application claims priority to and benefit under 35 U.S.C. § 119(e) of U.S. Provisional Patent Application Ser. No. 62/202,003, filed Aug. 6, 2015, U.S. Provisional Patent Application Ser. No. 62/208,217, filed Aug. 21, 2015, and U.S. Provisional Patent Application Ser. No. 62/362,813, filed Jul. 15, 2016, the contents of each of which are hereby incorporated by reference in their entirety as if fully set forth below.

FIELD

The present disclosure relates to water dispersible or soluble diagnostic assay methods, devices, methods of manufacture, and kits.

BACKGROUND

The field of rapid diagnostic testing has developed to permit the detection of analytes in a variety of sample types. The use of polyclonal antibodies was followed by the use of monoclonal antibodies to generate assays with high specificity for a number of analytes, including hormones, cells, drugs and their metabolites, as well as the antigens of infectious agents. The visible signal generated by enzyme-catalyzed reactions or by the accumulation of a visible signal at the level of a test line has also resulted in rapid development of highly sensitive results. Many of the rapid immunoassay-based tests include a solid housing encasing a test strip.

Existing devices typically comprise at least two parts: a rigid structure to serve as a support for the device, and a testing strip that carries out the test itself. Urine-based diagnostics usually fall into the categories of midstream (device is held in flowing stream of fluid), dip (device is held in stationary fluid sample), and cassette (dropper is used to add fluid sample), or top down assay. Such devices use rigid body structures, an imprecise specimen collection method (sometimes requiring counting from the user), and singular abstract readout per testing strip (in non-electronic devices). Compositions of current devices can include materials such as plastics, waxes, polymer layers, nitrocellulose, and woven layers (e.g., strips or other matrixes) that are not biodegradable and must be disposed of as trash. Further, each test strip component may be manufactured separately and subsequently assembled using batch processing, which increases transportation time, manufacturing time, equipment costs, and labor costs.

Because these diagnostic devices are often used to obtain sensitive test results, discretion is typically an important priority for the user. For example, discretion at disposal can be particularly important where one would not want a used device to be found.

The solutions presented herein address these and other needs in the art.

SUMMARY

A diagnostic device is provided in frequent embodiments provided herein comprising a test strip positioned in contact with a support, wherein the test strip and the support are each comprised of a water-dispersible material. Often, the test strip comprises a test zone and is in fluid communication with a sample zone and an absorbent zone, wherein the sample zone and the absorbent zone are comprised of a water-dispersible material. Also often, the water dispersible material is a water-dispersible matrix material. The test strip is frequently encased within the support. The support is also often treated with a hydrophobic solution.

In frequent embodiments, the support comprises an opening or window adjacent the sample zone or the test zone. The window is often positioned adjacent the test zone and comprises a dispersible or dissolvable but optically clear material such as Gelatine.

The support in frequent embodiments comprises one or more slit or one or more hole therein, wherein the slit or hole is configured to facilitate water dispersion of the matrix material. Also the support often comprises an embossed portion. A vent portion or raised portion for venting is also a frequent aspect of the support. Embossing may also be provided on the sample zone, test strip, and/or absorbent zone.

The test zone often comprises a test line and a control line on the matrix material, each line comprising an antibody. The antibody reagent, in often included embodiments, comprises a sugar and an antibody is releasably deposited on the test strip, wherein the antibody is specific for an analyte. The sugar often comprises trehalose and sucrose.

In particularly frequent embodiments, the device or test strip (including relevant aspects thereof) is configured to detect an analyte comprising human chorionic gonadatropin (hCG).

A diagnostic device is also provided herein comprising a test strip positioned in contact with a gelatin or collagen support, wherein the test strip and the support each disperse or dissolve in water. The test strip is often comprised in a diagnostic channel positioned in the support. The diagnostic channel is often lined with a hydrophobic water dispersible matrix material. And, the hydrophobic water dispersible matrix material is most frequently temporarily hydrophobic in the presence of a liquid sample. This hydrophobic water dispersible matrix material is in the most commonly included embodiments, treated with a hydrophobic solution. The test strip itself comprises a water dispersible matrix material and the device often further comprises a sample zone or absorbent zone in fluid communication with the diagnostic channel. The test strip often includes a test zone comprising a test line or a control line on the matrix material, each line comprising an antibody. In particularly frequent embodiments, the device or test strip (including relevant aspects thereof) is configured to detect an analyte comprising human chorionic gonadatropin (hCG).

In certain embodiments, a diagnostic device is provided comprising a label zone comprised of a water dispersible matrix material and at least one additional component in fluid communication with the label zone selected from the group consisting of a sample receiving zone, a test region (also referred to herein as a "test zone"), and an absorbent zone, wherein the label zone comprises a labeled reagent and a water dispersible or soluble coating agent. Frequently, the device comprises the label zone, the test region, and optionally the sample receiving zone and/or the absorbent zone. Often, if present, the label zone, the sample receiving zone, the test region, and the absorbent zone are comprised of a water dispersible matrix material. Frequently, the water dispersible matrix material comprises a water dispersible matrix sandwich material (WDMSM; also simply referred to herein as a matrix material or water dispersible matrix material). In certain frequent embodiments, the device is comprised of a single, contiguous water dispersible matrix material.

Often, the water dispersible matrix material comprises one or more flow paths. Also often, the water dispersible matrix material comprises two or more flow paths. Frequently, each of the two or more flow paths is not in fluid communication with one or more of another of the two or more flow paths. In certain frequent embodiments, one or more sample receiving zones is in fluid communication with each of the two or more flow paths. Often, one or more absorbent zones is in fluid communication with each of the two or more flow paths. Also often, each flow path comprises a sample receiving zone and/or an absorbent zone.

In certain frequent embodiments, the coating agent comprises a wet-strength resin, polyvinyl alcohol (PVA), polyamide-epichlorohydrin (PAE), a propylene glycol alginate (PGA), collagen, gelatin, a dissolvable film, polyethylene glycol (PEG), a water soluble silicone, a silica gel, a non-silica sol gel, a hydrogel, a water-dispersible or soluble wax, another water soluble or dispersible coating, or a combination of two or more of the foregoing.

Often, the labeled reagent is positioned between the coating agent and the water dispersible matrix material. Also often, the water soluble coating agent is positioned between the labeled reagent and the water dispersible matrix material. Frequently, the labeled reagent is positioned between a first layer and a second layer of the water soluble coating agent. In certain embodiments, the water soluble coating agent comprises two or more layers of water soluble coating agent, wherein the labeled reagent comprises two or more labeled reagents, wherein each of the two or more labeled reagents is separated from another of the two or more labeled reagents by at least a portion of a layer of one of the two or more layers of water soluble coating agent. Often, the two or more labeled reagents comprises the same or different labeled reagents, and the two or more layers of water soluble coating agent comprise the same or different water soluble coating agent. Often, the first layer is a different water soluble coating agent than the second layer.

In certain embodiments, the water soluble coating agent comprises a layer between about 0.25 µm-1.0 mm in thickness. Also, in certain embodiments, the water soluble coating agent comprises a layer between 1.0 mm to about 5.0 mm in thickness. In addition, in certain embodiments, the water soluble coating agent becomes soluble and dissolves in less than about 60 second when contacted with a target sample. In other certain embodiments, the water soluble coating agent becomes soluble and dissolves in between about 60 seconds to about 10 minutes when contacted with a target sample. Often, the dispersion or dissolution occurs within 24 hours. Also often, the dispersion or dissolution occurs within a week or a month after the device is contacted with a sample or water. In certain embodiments, including those incorporating a coating-based matrix, the dispersion or dissolution occurs within three to six months.

In certain frequent embodiments, the water soluble coating agent and/or the labeled reagent are positioned on the device in a dot matrix style and positioned in discreet dots or positioned on the device in one or more thin line(s).

In certain frequent embodiments, at least one of the one or more flow paths is a non-linear flow path. Often, one or more of the two or more flow paths is a non-linear flow path.

In certain embodiments, methods are provided for preparing a water dispersible label zone for an immunoassay, comprising contacting a water dispersible matrix material with a labeled reagent and a water soluble coating agent.

Often the water dispersible matrix material comprises a water dispersible matrix sandwich material (WDMSM). Also often, the label zone is positioned in a diagnostic device and the diagnostic device is comprised of a water dispersible matrix material. In frequent embodiments, the water dispersible matrix material of the label zone is positioned in contiguous non-overlapping fluid communication with the water dispersible matrix material of the diagnostic device.

Often, the water soluble coating agent in such methods comprises a wet-strength resin, polyvinyl alcohol (PVA), polyamide-epichlorohydrin (PAE), a propylene glycol alginate (PGA), collagen, gelatin, a dissolvable film, polyethylene glycol (PEG), a water soluble silicone, a silica gel, a non-silica sol gel, a hydrogel, a water-dispersible wax, another water soluble or dispersible coating, or a combination of two or more of the foregoing. Frequently, the labeled reagent is positioned between the water soluble coating agent and the water dispersible matrix material. Also frequently, the water soluble coating agent is positioned between the labeled reagent and the water dispersible matrix material. Often, the labeled reagent is positioned between a first layer and a second layer of the water soluble coating agent. Also often, the water soluble coating agent comprises two or more layers of water soluble coating agent, wherein the labeled reagent comprises two or more labeled reagents, wherein each of the two or more labeled reagents is separated from another of the two or more labeled reagents by at least a portion of a layer of one of the two or more layers of water soluble coating agent. Frequently, the two or more labeled reagents comprises the same or different labeled reagents, and the two or more layers of water soluble coating agent comprise the same or different water soluble coating agent. Often, the first layer is a different water soluble coating than the second layer.

In certain methods, the water soluble coating comprises a layer between about 0.25 µm-1.0 mm in thickness. The water soluble coating may also comprise a layer between about 1.0 mm-5.0 mm in thickness. Often, the water soluble coating becomes soluble and dissolves in less than about 60 second when contacted with a target sample. Also often, the water soluble coating agent becomes soluble and dissolves in between about 60 seconds to about 10 minutes when contacted with a target sample. Often, the dispersion or dissolution occurs within 24 hours. Also often, the dispersion or dissolution occurs within a week or a month after the method is conducted. In certain embodiments, including those incorporating a coating-based matrix, the dispersion or dissolution occurs within three to six months.

In certain embodiments, the water soluble coating and/or the labeled reagent are positioned on the device in a dot matrix style and positioned in discreet dots or positioned on the device in one or more thin line.

In certain frequent embodiments, a kit is provided comprising a device described herein and a packaging material or instructions. Often, the kit further comprising a desiccant. In certain embodiments, the desiccant is a soluble or dispersible coating. Often, the packaging material comprises an oxygen free environment. Frequently, often the packaging material is comprised of a water dispersible material. Also frequently, the packaging material is comprised of a biodegradable material.

In one embodiment, a method for forming an axial flow diagnostic device can include dispensing at least one reagent over, on, and/or within a matrix, wherein the matrix is at least one of water soluble and water dispersible after use of the axial flow diagnostic device.

A method for forming an axial flow diagnostic device can include, for example, providing a web comprising at least one matrix layer, dispensing at least one reagent over, on, and/or within the web, and segmenting the web into a plurality of individual matrix sections, wherein the matrix is at least one of water soluble and water dispersible after use of the axial flow diagnostic device. Often the method comprises forming at least one reagent channel over, on, or within the matrix; and dispensing the at least one reagent into the at least one reagent channel. In frequent embodiments, the method comprises forming the at least one reagent channel using at least one method selected from the group comprising embossing the matrix, ink-jet printing a layer onto the matrix, laser cutting the matrix, laminating a patterned first matrix layer having one or more channel openings therein onto a second matrix layer, and stamping the matrix. Often, a collection pad is formed from the matrix, wherein the collection pad comprises a plurality of fluid diversion conduits configured to direct a fluid toward the at least one reagent channel.

Such methods often comprise a step or process (including equipment related thereto) of embossing the plurality of fluid diversion conduits into the collection pad. The matrix often has a first surface area and the method further comprises forming a collection pad from the matrix, wherein the collection pad comprises a second surface area that is higher than the first surface area. In certain embodiments, the method comprises embossing the matrix to form the collection pad.

Manufacturing methods may often include a curing step to cure reagents on the matrix, for example, using a heat source. Manufacturing methods may also employ cutting the matrix to segment the matrix into a plurality of individual matrix sections. In certain embodiments, the methods comprise laminating a first matrix layer and a second matrix layer together to form the matrix.

In certain embodiments, at least one reagent is placed onto and/or over the first matrix layer; then laminating is performed, thereby interposing the at least one reagent between the first matrix layer and the second matrix layer.

Also in certain embodiments, a method for forming an axial flow diagnostic device is provided, comprising: dispensing at least one reagent over, on, and/or within a web comprising at least one matrix layer; and segmenting the web into a plurality of individual matrix sections, wherein the matrix is at least one of water-soluble and water-dispersible after use of the axial flow diagnostic device. In certain embodiments, the method may comprise embossing a first portion of the web to form at least one reagent channel; and dispensing the at least one reagent into the at least one reagent channel. In certain embodiments, the method may comprise embossing a second portion of the web to form a plurality of fluid diversion conduits configured to direct a fluid toward the at least one reagent channel. In certain embodiments, the method may comprise placing the at least one reagent onto a first matrix layer; and laminating the first matrix layer to at least a second matrix layer to form the web, wherein the at least one reagent is interposed between the first matrix layer and the second matrix layer. In certain embodiments, the method may comprise removing a plurality of matrix layers, including the at least one matrix layer, from a plurality of reels; and laminating the plurality of matrix layers together to form the web.

The device or matrix is often packaged after manufacture, for example, by placing the matrix and the at least one reagent within a pouch, wherein the pouch is water-soluble and/or water-dispersible. Often, a desiccant is placed and/or sealed within the pouch. Additional methods of manufacture are specifically detailed herein. The manufacturing process may include printing or placing an indicia onto the matrix, where the indicia comprises at least one of text and graphics.

As indicated, the device or test strip (including relevant aspects thereof) is often configured to detect an analyte comprising human chorionic gonadatropin (hCG).

These and other embodiments, features, and advantages will become apparent to those skilled in the art when taken with reference to the following more detailed description of various exemplary embodiments of the present disclosure in conjunction with the accompanying drawings.

BRIEF DESCRIPTION OF THE DRAWINGS

The skilled person in the art will understand that the drawings, described below, are for illustration purposes only. The drawings are incorporated in and constitute a part of this specification.

FIG. 13A depicts a line drawing of another exemplary device, including its various aspects.

FIG. 13B depicts a line drawing of an embodiment of a sample receiving zone of an exemplary device.

FIG. 13C depicts a line drawing of an embodiment of an absorbent zone of an exemplary device.

FIG. 14A depicts a line drawing of another exemplary device, including its various aspects.

FIG. 14B depicts a line drawing of an embodiment of a combined sample receiving zone and test strip of an exemplary device.

FIG. 14C depicts a line drawing of an embodiment of an absorbent zone of an exemplary device.

FIG. 16A depicts a line drawing of another exemplary device, including its various aspects.

FIG. 16B depicts a line drawing of an embodiment of a sample receiving zone, test strip, and absorbent zone of an exemplary device.

DETAILED DESCRIPTION OF THE VARIOUS EMBODIMENTS

Figure 1:
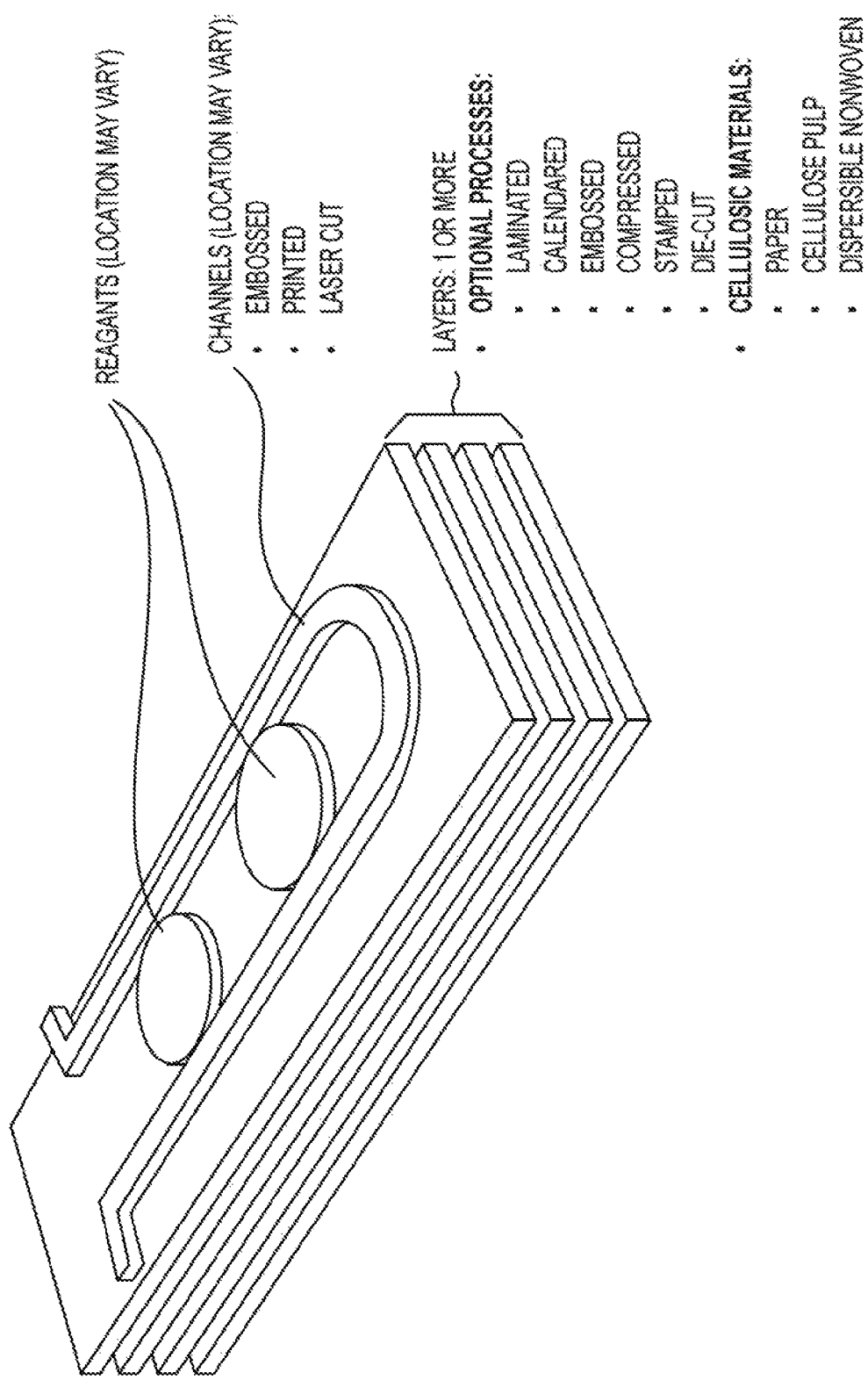
FIG. 1 is a perspective depiction of a diagnostic test device formed in accordance with an embodiment of the present teachings.

For clarity of disclosure, and not by way of limitation, the detailed description of the various embodiments is divided into certain subsections that follow.

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, the term "and/or" may mean "and," it may mean "or," it may mean "exclusive-or," it may mean "one," it may mean "some, but not all," it may mean "neither," and/or it may mean "both."

As used herein, the terms "detect," "detecting," or "detection" may describe either the general act of discovering or discerning or the specific observation of a molecule or composition, whether directly or indirectly.

As used herein, "antigen" refers to any compound capable of binding to an antibody, or against which antibodies can be raised.

As used herein, "antibody" refers to a polypeptide substantially encoded by an immunoglobulin gene or immunoglobulin genes, or fragments thereof. The recognized immunoglobulin genes include the kappa, lambda, alpha, gamma, delta, epsilon, and mu constant regions, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD, and IgE, respectively. Typically, an antibody is an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof. Fragments thereof may include Fab, Fv and F(ab')2, Fab', and the like. Antibodies may also include chimeric antibodies or fragment thereof made by recombinant methods.

As used herein, "monoclonal antibody" refers to an antibody obtained from a population of substantially homogeneous antibodies, i.e., the antibodies comprising the population are identical except for possible naturally occurring mutations that are present in minor amounts.

As used herein, the term "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues comprise an aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

"Fluid sample" or "liquid sample" refers to a material suspected of containing the analyte(s) of interest, which material has sufficient fluidity to flow through an immunoassay device in accordance herewith. The fluid sample can be used as obtained directly from the source or following a pretreatment so as to modify its character. Such samples can include human, animal or man-made samples. The sample can be prepared in any convenient medium which does not interfere with the assay. Typically, the sample is an aqueous solution or biological fluid as described in more detail below.

The fluid sample can be derived from any source, such as a physiological fluid, including blood, serum, plasma, saliva, sputum, ocular lens fluid, sweat, urine, milk, ascites fluid, mucous, synovial fluid, peritoneal fluid, transdermal exudates, pharyngeal exudates, bronchoalveolar lavage, tracheal aspirations, cerebrospinal fluid, semen, cervical mucus, vaginal or urethral secretions, amniotic fluid, and the like. Herein, fluid homogenates of cellular tissues such as, for example, hair, skin and nail scrapings, meat extracts and skins of fruits and nuts are also considered biological fluids. Pretreatment may involve preparing plasma from blood, diluting viscous fluids, and the like. Methods of treatment can involve filtration, distillation, separation, concentration, inactivation of interfering components, and the addition of reagents. Besides physiological fluids, other samples can be used such as water, food products, soil extracts, and the like for the performance of industrial, environmental, or food production assays as well as diagnostic assays. In addition, a solid material suspected of containing the analyte can be used as the test sample once it is modified to form a liquid medium or to release the analyte. The selection and pretreatment of biological, industrial, and environmental samples prior to testing is well known in the art and need not be described further.

As used herein, the term "specifically binds" refers to the binding specificity of a specific binding pair. Recognition by an antibody of a particular target in the presence of other potential targets is one characteristic of such binding. "Binding component member" refers to a member of a specific binding pair, i.e., two different molecules wherein one of the molecules specifically binds with the second molecule through chemical or physical means. The two molecules are related in the sense that their binding with each other is such that they are capable of distinguishing their binding partner from other assay constituents having similar characteristics. The members of the binding component pair are referred to as ligand and receptor (antiligand), specific binding pair (sbp) member and sbp partner, and the like. A molecule may also be a sbp member for an aggregation of molecules; for example an antibody raised against an immune complex of a second antibody and its corresponding antigen may be considered to be an sbp member for the immune complex.

In addition to antigen and antibody binding component members, other binding components include, as examples without limitation, biotin and avidin, carbohydrates and lectins, complementary nucleotide sequences, complementary peptide sequences, effector and receptor molecules, enzyme cofactors and enzymes, enzyme inhibitors and enzymes, a peptide sequence and an antibody specific for the sequence or the entire protein, polymeric acids and bases, dyes and protein binders, peptides and specific protein binders (e.g., ribonuclease, S-peptide and ribonuclease S-protein), metals and their chelators, and the like. Furthermore, binding components can include members that are analogs of the original binding component member, for example an analyte-analog or a binding component member made by recombinant techniques or molecular engineering.

An sbp member is analogous to another sbp member if they are both capable of binding to another identical complementary sbp member. Such an sbp member may, for example, be either a ligand or a receptor that has been modified by the replacement of at least one hydrogen atom by a group to provide, for example, a labeled ligand or labeled receptor. The sbp members can be analogous to or complementary to the analyte or to an sbp member that is complementary to the analyte.

If the binding component is an immunoreactant it can be, for example, an antibody, antigen, hapten, or complex thereof. If an antibody is used, it can be a monoclonal or polyclonal antibody, a recombinant protein or antibody, a chimeric antibody, a mixture(s) or fragment(s) thereof, as well as a mixture of an antibody and other binding component members. The details of the preparation of such antibodies and their suitability for use as specific binding members are known to those skilled in the art.

"Analyte" refers to the compound or composition to be detected or measured and which has at least one epitope or binding site. The analyte can be any substance for which there exists a naturally occurring analyte specific binding member or for which an analyte-specific binding member or antibody can be prepared.

Analytes include, but are not limited to, toxins, organic compounds, proteins, peptides, microorganisms, bacteria, viruses, amino acids, nucleic acids, carbohydrates, hormones, steroids, vitamins, drugs (including those administered for therapeutic purposes as well as those administered for illicit purposes), pollutants, pesticides, and metabolites of or antibodies to any of the above substances. The term analyte also includes any antigenic substances, haptens, antibodies, macromolecules, and combinations thereof. A non-exhaustive list of exemplary analytes is set forth in U.S. Pat. No. 4,366,241, at column 19, line 7 through column 26, line 42, the disclosure of which is incorporated herein by reference. Further descriptions and listings of representative analytes are found in U.S. Pat. Nos. 4,299,916; 4,275,149; and 4,806,311, all incorporated herein by reference. Certain specifically contemplated analytes include α-hCG, β-hCG, progesterone, luteinizing hormone, etc.

"Labeled reagent" refers to a substance comprising a detectable label attached with a specific binding member. The attachment may be covalent or non-covalent binding, but the method of attachment is not critical to the present invention. The label allows the label reagent to produce a detectable signal that is related to the presence of analyte in the fluid sample. The specific binding member component of the label reagent is selected to directly bind to the analyte or to indirectly bind the analyte by means of an ancillary specific binding member, which is described in greater detail hereinafter. The label reagent can be incorporated into the test device at a site upstream from the capture zone, it can be combined with the fluid sample to form a fluid solution, it can be added to the test device separately from the test sample, or it can be predeposited or reversibly immobilized at the capture zone. In addition, the specific binding member may be labeled before or during the performance of the assay by means of a suitable attachment method.

"Label" refers to any substance which is capable of producing a signal that is detectable by visual or instrumental means. Often, a label refers to a latex bead, gold particle, or cellulose nanobead, each of which is conjugated to an antibody or portion thereof. Various labels suitable for use in the present invention include labels which produce signals through either chemical or physical means. Such labels can include enzymes and substrates, chromogens, catalysts, fluorescent compounds, chemiluminescent compounds, and radioactive labels. Other suitable labels include particulate labels such as colloidal metallic particles such as gold, colloidal non-metallic particles such as selenium or tellurium, dyed or colored particles such as a dyed plastic or a stained microorganism, organic polymer latex particles and liposomes, colored beads, polymer microcapsules, sacs, erythrocytes, erythrocyte ghosts, or other vesicles containing directly visible substances, and the like. Typically, a visually detectable label is used as the label component of the label reagent, thereby providing for the direct visual or instrumental readout of the presence or amount of the analyte in the test sample without the need for additional signal producing components at the detection sites.

Generally, the label will be capable of generating a detectable signal either by itself, or be instrumentally detectable, or be detectable in conjunction with one or more additional signal producing components, such as an enzyme/substrate signal producing system. A variety of different label reagents can be formed by varying either the label or the specific binding member component of the label reagent; it will be appreciated by one skilled in the art that the choice involves consideration of the analyte to be detected and the desired means of detection. As discussed below, a label may also be incorporated used in a control system for the assay.

For example, one or more signal producing components can be reacted with the label to generate a detectable signal. If the label is an enzyme, then amplification of the detectable signal is obtained by reacting the enzyme with one or more substrates or additional enzymes and substrates to produce a detectable reaction product.

In an alternative signal producing system, the label can be a fluorescent compound where no enzymatic manipulation of the label is required to produce the detectable signal. Fluorescent molecules include, for example, fluorescein, phycobiliprotein, rhodamine and their derivatives and analogs are suitable for use as labels in such a system.

The use of dyes for staining biological materials, such as proteins, carbohydrates, nucleic acids, and whole organisms is documented in the literature. It is known that certain dyes stain particular materials preferentially based on compatible chemistries of dye and ligand. For example, Coomassie Blue and Methylene Blue for proteins, periodic acid-Schiffs reagent for carbohydrates, Crystal Violet, Safranin O, and Trypan Blue for whole cell stains, ethidium bromide and Acridine Orange for nucleic acid staining, and fluorescent stains such as rhodamine and Calcofluor White for detection by fluorescent microscopy. Further examples of labels can be found in, at least, U.S. Pat. Nos. 4,695,554; 4,863,875; 4,373,932; and 4,366,241, all incorporated herein by reference.

"Signal producing component" refers to any substance capable of reacting with another assay reagent or with the analyte to produce a reaction product or signal that indicates the presence of the analyte and that is detectable by visual or instrumental means. "Signal production system", as used herein, refers to the group of assay reagents that are needed to produce the desired reaction product or signal.

"Observable signal" as used herein refers to a signal produced in the claimed devices and methods that is detectable by visual inspection. Without limitation, the type of signal produced depends on the label reagents and marks used (described herein). Generally, observable signals indicating the presence or absence of an analyte in a sample may be evident of their own accord, e.g., plus or minus signs or particularly shaped symbols, or may be evident through the comparison with a panel such as a color indicator panel.

"Axial flow" as used herein refers to lateral, vertical or transverse flow through a particular matrix or material comprising one or more test and/or control zones. The type of flow contemplated in a particular device, assay or method varies according to the structure of the device. Without being bound by theory, lateral, vertical or transverse flow may refer to flow of a fluid sample from the point of fluid contact on one end or side of a particular matrix (the upstream or proximal end) to an area downstream (or distal) of this contact. The downstream area may be on the same side or on the opposite side of the matrix from the point of fluid contact.

As used herein the terms "upstream" and "downstream" refer to the direction of fluid sample flow subsequent to contact of the fluid sample with a representative device of the present disclosure, wherein, under normal operating conditions, the fluid sample flow direction runs from an upstream position to a downstream position. For example, when fluid sample is initially contacted with the sample receiving zone, the fluid sample then flows downstream through the label zone and so forth.

As used herein the phrase "completion of an assay" refers to axial flow of applied liquid sample suspected of containing one or more analytes through a representative device, downstream of at least one test zone and at least one control zone. More commonly, the phrase completion of assay refers to axial flow of applied liquid sample suspected of containing one or more analytes through a representative device, downstream of all test and control zones on or in the device.

As used herein the term "dispersible" means that the fibers of a material are capable of debonding, resulting in the material breaking down into smaller pieces than the original sheet. Debonding is generally a physical change of scattering or separation, as compared to a state change, such as dissolving, wherein the material goes into solution, e.g., a water soluble polymer dissolving in water.

As used herein the term "soluble" has a conventional meaning. In other words, "soluble" refers to the ability of a specified material to dissolve in another substance such as water, a fluid sample, or another fluid.

As used herein, the phrase "fibrous nonwoven composite structure" refers to a structure of individual fibers or filaments with or without particulates which are interlaid, but not in an identifiable repeating manner. Nonwoven structures such as, for example, fibrous nonwoven webs have been formed in the past, by a variety of processes known to those skilled in the art including, for example, meltblowing and meltspinning processes, spunbonding processes, bonded carded web processes, hydroentangling, and the like. Traditional methods of forming a nonwoven web comprising the matrix are contemplated (e.g., as described in U.S. Patent App. Pub. no. 20140170402), in addition to other methods such as, for example, electrospinning using fibers formed of all or a portion of hybrophobic fibers or formed another way As used herein, "fluid communication" refers to the disposition or arrangement of a material or materials such that fluid is able to flow through the material (e.g., matrix material) or flow between materials via capillary action, bibulous flow, axial flow, or non-bibulous flow. A material can be in "fluid communication" with another material regardless of the presence of fluid if it provides the capability to permit the flow of fluid between materials when fluid is present.

As used herein "test strip" refers to a portion of an exemplary device comprising a test region, and also optionally in fluid communication with a sample receiving zone and/or absorbent zone. A test strip may comprise or be connected with a label zone and may comprise one or more flow paths. A test strip may also, in certain contemplated embodiments, be comprised of or in the same contiguous matrix material that forms a sample receiving zone and/or absorbent zone.

As used herein "contiguous matrix material" refers to a single sheet of matrix material.

As used herein, the term "water dispersible" refers to a fibrous nonwoven composite structure that, when placed in an aqueous environment will (over time) break apart into smaller pieces. Once the structure is broken apart and dispersed, it is processable in recycling processes, for example, septic and municipal sewage treatment systems. If desired, the fibrous nonwoven structures can be made more water-dispersible or the dispersion can be quickened. The actual amount of time for dispersion can vary and be predetermined based on the intended use profile. In frequent embodiments, the water dispersible or soluble matrix materials contemplated herein disperse in water and pass flushablity guidelines of INDA and EDANA.

As used herein, "flushable" refers to materials that disperse in water and pass the flushablity guidelines of INDA and/or EDANA, for example, as set forth in "Guidelines for Assessing the Flushability of Disposable Nonwoven Products," Third Edition, August 2013, INDA and EDANA.

As used herein, the term "matrix material" (including non-synthetic matrix material, water dispersible or soluble matrix material, water dispersible matrix sandwich material, etc.) excludes nitrocellulose and nitrocellulose material. Most frequently, this matrix material comprises a flushable, water dispersible, biodegradable, and/or soluble matrix material such as a nonwoven web material. The term "matrix material" is also intended to refer to the material regardless of whether it has been treated with a coating or lamination.

As used herein, "sample receiving zone" (also referred to as a "sample zone" or "sample pad") refers to a portion where a sample is contacted with a device contemplated herein. This zone may include or comprise a sample pad that is specifically adapted for contact with a liquid sample.

As used herein, "absorbent zone" (also referred to as an "absorbent pad") refers to a portion where a sample passes or is absorbed into after passing through a test zone.

As used herein, "support" is intended to encompass the term "housing" as one form of, or way of referring to, a specifically contemplated support.

Other features and advantages of the invention will be apparent from the following description and referenced drawings. The present innovations are often further described by examples. The examples are provided solely to illustrate the innovations by reference to specific embodiments. The drawings, which are not necessarily to scale, depict selected embodiments and are not intended to limit the scope of the present disclosure. These exemplifications, while illustrating certain specific aspects of the innovations, do not portray the limitations or circumscribe the scope of the disclosed innovations. The detailed description illustrates by way of example, and is not intended to limit the scope of the present disclosure.

The present disclosure contemplates the use of water dispersible or soluble matrix materials having axial flow capabilities.

The water dispersible or soluble matrix materials contemplated herein provide, for example, a seamless and environmentally sustainable manufacturing process and use protocol. In particular, in frequent embodiments, a water dispersible or soluble matrix material is utilized to constitute multiple components/aspects of the contemplated devices, as constituting the entire flow path of the device, or as constituting the entire device apart from reagents. Traditional lateral flow assay devices typically utilize nitrocellulose, mylar, laminate cover, backing card, desiccant, conjugate pad, strip housing or casette, absorbent zone, sample collection area, sample receiving zone, detection conjugate, test and/or control reagent lines. Embodiments provided herein utilize a water dispersible or soluble matrix material for one or more, or two or more, of these components. In certain embodiments, the entire flow path of the device is comprised of a single water dispersible or soluble matrix material such that sample, reagent, and analyte flow occurs within a single contiguous matrix, or a single matrix type.

One exemplary material contemplated herein as a water dispersible matrix is a nonwoven fabric material called HYDRASPUN® (Suominen, Helsinki, FI). Though not wishing to be bound by any particular theory of operation, characteristics of this material that are utilized in the presently contemplated methods and devices are an increased resistance to water-dispersion. In other words, this material is and can be characterized as absorbent. Such water dispersible or soluble matrix materials are often referred to herein as water dispersible matrix sandwich materials ("WDMSM"). In certain embodiments, the nonwoven fabric material comprises water content of less than about 10% by weight. In certain embodiments, the water dispersible or soluble matrix material comprises a dry tri-layered material having an internal layer of, for example, cellulose pulp fibers, an upper layer of said continuous filaments of a water-soluble or water-dispersible polymer and a lower layer of said continuous filaments of a water-soluble or water-dispersible polymer. Other water dispersible or soluble matrix materials are contemplated and described, for example, in U.S. Pat. Nos. 4,309,469, 4,419,403, 5,952,251, and/or 8,668,808. SOFTFLUSH® (Jacob Holm & Sons AG) and NBOND® (Hangzhou Nbond Nonwoven Co., Ltd. Corp.) are additional examples of WDMSM materials. In certain embodiments, a WDMSM refers to layered or sandwiched coating materials, and particularly to a layered coating or coatings defining one or more microfluidic channels.

Properties of certain contemplated water dispersible or soluble matrix materials are set forth below. The materials were prepared prior to water/sample introduction with a dried visible dye reagent.

|  | WDMSM | Thick Cellulose | Handsheet |
| --- | --- | --- | --- |
| General Wicking Speed | Fast | Slow | Fast |
| Slow down Wicking Speed with Narrow Test | Yes | Yes | Yes |
| Dried Dye into Solution | Yes - with leading edge of water | Some | Yes |
| Dye flow speed | Fast | Very slow | Slow |
| Uniform Dye Flow | Yes | No | No |

The WDMSM material provided optimal results for permitting solutions to flow in a consistent or predictable manner. Dye was previously dried down on the materials and was pulled through the WDMSM material completely and consistently. The flow rate slowed through the narrow test strip area. This decrease in flow rate is found to be useful to permit enough time for any analytes (e.g., hCG) in a sample to bind to the ligand such as a conjugated antibody, and flow to a test region on the device. WDMSM was found to generally display good wicking ability with normal sample volumes. Wicking speed in WDMSM can be controlled, for example, by using thicker fabric or by narrowing the test strip area of the device. It was also found that a larger sample volume is well tolerated and provides consistent saturation times. With regard to cellulose, water (e.g., deionized water or "DIW") wicks through the thick cellulose fabric (e.g., CelluFlex® available from Georgia-Pacific LLC, Atlanta, Ga.), but wicking is much slower than WDMSM. It was also found that fabric thickness reduces the forward motion of the DIW through the test strip in cellulose.

Components of traditional devices include a sample collection area, a sample receiving zone, a conjugate pad, a nitrocellulose membrane, an absorbent zone, a backing card, a laminate cover tape, and a housing/cassette. It is contemplated herein in certain limited embodiments that traditional devices having such components, including dipstick, lateral flow and flow-through devices are modified in order to substitute device materials contemplated herein. Exemplary lateral flow devices include those described in U.S. Pat. Nos. 4,818,677, 4,943,522, 5,096,837, 5,096,837,5,118,428, 5,118,630, 5,221,616, 5,223,220, 5,225,328, 5,415,994, 5,434,057, 5,521,102, 5,536,646, 5,541,069, 5,686,315, 5,763,262, 5,766,961, 5,770,460, 5,773,234, 5,786,220, 5,804,452, 5,814,455, and 5,939,331, 6,306,642. Other lateral flow devices that may be modified for use in distinguishable detection of multiple analytes in a fluid sample, including those provided in U.S. Pat. Nos. 4,703,017, 6,187, 598, 6,352,862, 6,485,982, 6,534,320 and 6,767,714. Exemplary dipstick devices include, for example, those described in U.S. Pat. Nos. 4,235,601, 5,559,041, 5,712,172 and 6,790,611. The presently contemplated devices generally do not utilize or incorporate nitrocellulose since nitrocellulose is not water dispersible, biodegradable, nor flushable.

In certain embodiments a sample collection area is provided that is often made from the same, non-synthetic matrix material (e.g., water dispersible or soluble matrix material) as other contiguous or separate components of the device, often includes embossing/patterning design for absorption and fluidic flow, and optionally includes a perforation or a mechanism to permit its removal from the device (for example, by tearing, cutting, or drawstring removal). In frequent embodiments, the sample receiving zone is also comprised of the same, non-synthetic matrix material (e.g., water dispersible or soluble matrix material) as other contiguous or separate components of the device.

In certain frequent embodiments, the conjugate pad is comprised of the same, non-synthetic matrix material (e.g., water dispersible or soluble matrix material) as other contiguous or separate components of the device. Optionally, in certain embodiments, a separate label zone comprising a conjugate pad type component is absent from presently described embodiments. Rather, reagent (e.g., conjugate) is often impregnated or positioned in or on the same non-synthetic matrix material as other aspects of the device. Though not wishing to be bound by any specific theory, the use of the presently contemplated materials for reagent positioning or impregnation permits for enhanced and shortened impregnation times compared with traditional glass fiber and polyester pads. In certain frequent embodiments, for example, the reagent such as conjugate is positioned in a material layer, portion, or plug of material positioned below a top layer of the non-synthetic matrix material. See, e.g., FIG. 5B. Often, in such embodiments, the reagent is positioned below the surface of the device. This differs significantly from traditional immersion or spray deposition techniques. In certain frequent embodiments, reagent such as a conjugate reagent (e.g., a labeled reagent) is positioned on, within, between, or below a coating material (described elsewhere herein) that is separate from the non-synthetic matrix material. See, e.g., FIGS. 4-7. Often, reagent such as conjugate reagent is positioned in a channel (i.e., a form of a flow path) formed on or in the device. See, e.g., FIGS. 5A, 6A. A coating may be positioned over the reagent and/or between the reagent and the matrix in or over the channel.

The presently described devices are provided without a traditional nitrocellulose membrane that is utilized in known devices as comprising the test region having test and control areas. Nitrocellulose membranes are synthetic and non-water dispersible or soluble. Instead, the presently described devices utilize a non-synthetic matrix material as comprising the test region. As used herein, the term "matrix material" (including non-synthetic matrix material, water dispersible or soluble matrix material, water dispersible matrix sandwich material, etc.) excludes nitrocellulose and nitrocellulose material. Most frequently, this matrix material comprises a water dispersible or soluble matrix material. This matrix material is frequently the same material as that which comprises the sample collection area and/or sample receiving zone, optionally in addition to the area containing reagent such as conjugate. Often, this matrix material is the same contiguous material as that which comprises the sample collection area and/or sample receiving zone, optionally in addition to the area containing reagent such as conjugate. The term "matrix material" is also intended to include materials having coatings, and particularly to a layered coating, lamination coatings, or coatings defining one or more microfluidic channels as described herein.

The presently contemplated devices provide, for example, an easier readability (e.g., analog, direct view, etc.) relative to nitrocellulose-based devices, achieved by using a larger reagent area and/or test region in addition to flow path and channel designs and material selections as described herein. Frequent devices provide a large area for strategic channel design (including shaping and direction) for ease in interpretation. Often, flow path channels are provided in a circuitous or non-linear route. In certain embodiments, the device is provided with both linear and non-linear channels. Also often, indicia are printed on the device to further enhance readability such as spelling out words or symbols specifically indicating the location and significance of each test or control line or portion such as "pregnant," "positive," "control," "device working," etc. When the matrix material is WDMSM, for example, this material is or becomes somewhat or partially transparent when wetted, which permits ease in visibility of test results such as those represented by chromatographic changes. Often, the traditional test or control lines are re-configured in the present devices to provide pictographic representations, words, or designs for at least one of the test or control result representation.

Rather than integrating a separate absorbent zone to collect sample as it passes through the test region, the present devices most frequently utilize an extension of the non-synthetic matrix material that comprises the test region (among other regions of the device or entire device) as the absorbent zone.

Devices of the present disclosure also often eliminate the need for a plastic backing card traditionally used in test strips. Rather, the same non-synthetic matrix material used in other aspects or components is used to provide rigidity and/or a fluid barrier to the device. Often, a non-synthetic matrix material that is water dispersible or soluble is used as a support material, which is often treated with a hydrophobic solution. In frequent embodiments, the non-synthetic matrix material used as a support is coated with a material or agent with limited, slow, or delayed wetability, for example, as taught in commonly owned U.S. Provisional Patent Application Ser. No. 62/362,813, filed Jul. 15, 2016 (the teachings of which are hereby incorporated by reference). Often, the non-synthetic matrix material as a support is a material with limited, slow, or delayed wetability. A second or other water dispersible or soluble material of increased rigidity versus the water dispersible or soluble matrix material, for example, is also frequently used. In certain embodiments, the device comprises two or more different water dispersible or soluble materials. In certain embodiments, the device comprises three or more different water dispersible or soluble materials. In certain embodiments the device comprises two of the same or similar water dispersible or soluble matrix materials and a second (e.g., different) water dispersible or soluble material sandwiched between the two same or similar water dispersible or soluble matrix materials. In such embodiments, the device is adapted to provide for the same or different assays on each of the two same or similar water dispersible or soluble matrix materials. Also, in such embodiments, each of the same or similar water dispersible or soluble matrix defines an individual flow path. Most frequently, when fluid enters one of the two individual flow-paths, or reaches a pre-determined location on the device, it does not pass through to the other of the two individual flow paths.

Devices of the present disclosure also often eliminate the need for a laminate or cover tape or polymer traditionally used in test strips, for example, either by substitution of a water-soluble and/or water dispersible or soluble coating, or in some instances, eliminating the need for such cover tape.

Devices of the present disclosure also often eliminate or forego the need or desire for a non-flushable plastic housing or cassette. In fact, the presence or use of non-flushable materials such as a plastic housing departs from a general theme of the present disclosure to provide for environmentally sensitive water-dispersible or soluble devices that permit a level of privacy not heretofore achievable. Plastic housings and non-flushable components such as test strips containing nitrocellulose must be disposed in solid waste containers. Moreover, plastic housings or cassettes prohibit discreet packaging of fully functional devices. In contrast, in many embodiments of the presently contemplated devices, the device itself is foldable to be stored in a small area. Usage merely entails unfolding and contacting a sample with the device.

In a frequent embodiment, the sample receiving zone (sample zone) accepts a fluid sample that may contain analytes of interest. In another embodiment, the sample receiving zone is dipped into a fluid sample. A label zone may be located downstream of the sample receiving zone but is also often positioned within the sample zone, and contains one or more mobile label reagents that recognize, or are capable of binding the analytes of interest. Further, a test region is disposed downstream from the sample zone, and often contains test and control zones or lines. The test zone(s) generally contain a reagent or adaptation that permits the restraint of a particular analyte of interest in each test zone. Frequently, the reagent or adaptation included in the test zone(s) comprises an immobilized capture reagent that binds to the analyte of interest. Generally the immobilized capture reagent specifically binds to the analyte of interest. Although, on occasion, the reagent or adaptation that permits the restraint of a particular analyte of interest in each test zone comprises another physical, chemical or immunological adaptation for specifically restraining an analyte of interest. Thus, as the fluid sample flows along the matrix, the analyte of interest will first bind with a mobilizable label reagent in the label zone, and then become restrained in the test zone. In occasional embodiments, the test region is comprised of a material that is opaque in a dry state and transparent in a moist state. Thus, when a control zone or line comprising a mark on the device is utilized, this mark is positioned about the test region such that it becomes visible within the test region when the test region is in a moist state.

Often, the fluid sample flows along a flow path running from the sample receiving zone (upstream), optionally the label zone is separate from the sample zone, and then to the test zone (downstream). Optionally, the fluid sample may thereafter continue to an absorbent zone.

The sample receiving zone is frequently comprised of an absorbent application pad such as a cellulose pad or HYDRASPUN®. In a related embodiment, the sample receiving zone is constructed from any material that is water dispersible or soluble yet capable of absorbing water.

Also often, the sample receiving zone is comprised of a water dispersible or soluble material from which the fluid sample can pass to the label zone. Often, the sample receiving zone acts as a filter for cellular components, hormones, particulate, and other certain substances that may be present in a fluid sample. The functions of the sample receiving zone may include, for example: pH control/modification and/or specific gravity control/modification of the sample applied, removal or alteration of components of the sample which may interfere or cause non-specific binding in the assay, or to direct and control sample flow to the test region. The filtering aspect allows an analyte of interest to migrate through the device in a controlled fashion with few, if any, interfering substances. The filtering aspect, if present, often provides for a test having a higher probability of success and accuracy. In another embodiment, the sample receiving zone may also incorporate reagents useful to avoid cross-reactivity with non-target analytes that may exist in a sample and/or to condition the sample; depending on the particular embodiment, these reagents may include non-hCG blockers, anti-RBC reagents, Tris-based buffers, EDTA, among others. When the use of whole blood is contemplated, anti-RBC reagents are frequently utilized. In yet another embodiment, the sample receiving zone may incorporate other reagents such as ancillary specific binding members, fluid sample pretreatment reagents, and signal producing reagents.

In frequent embodiments, the sample receiving zone is comprised of an additional sample application member (e.g., a wick). Thus, in one aspect, the sample receiving zone can comprise a sample application pad as well as a sample application member. Often, the sample application member is comprised of a water dispersible or soluble material that readily absorbs any of a variety of fluid samples contemplated herein, and remains robust in physical form throughout the duration or initiation of an assay. The sample application member, if present, is positioned in fluid-flow contact with a sample application pad or another zone of the flow path of the device. This fluid flow contact can comprise a contiguous, overlapping, abutting or interlaced type of contact. Often the sample application member, if present, may contain similar reagents and be comprised of similar materials to those utilized in exemplary sample application pads.

In another embodiment, the test device is configured to perform an immunological analysis process. In yet another embodiment, the liquid transport along the matrix is based upon capillary action. In a further embodiment, the liquid transport along the matrix is based on non-bibulous lateral flow, wherein all of the dissolved or dispersed components of the liquid sample are carried at substantially equal rates and with relatively unimpaired flow laterally through the matrix, as opposed to preferential retention of one or more components as would occur, e.g., in materials that interact, chemically, physically, ionically or otherwise with one or more components.

One purpose of the label zone is to maintain label reagents and/or control reagents in a stable state and to facilitate their rapid and effective solubilization, mobilization and specific reaction with analytes of interest potentially present in a fluid sample.

In one embodiment, the label zone is comprised of a HYRDRASPUN®, cellulose, or other water dispersible or soluble matrix material. Often, the label zone comprises a fluid resistant backing material or coating to inhibit or slow the seepage of fluid therethrough. Most frequently the water resistant backing material or coating is water dispersible or soluble. The label zone may be constructed to provide either bibulous or non-bibulous flow, frequently the flow type is similar or identical to that provided in at least a portion of the sample receiving zone.

In a frequent embodiment, the label zone material is treated with labeled solution that includes material-blocking and label-stabilizing agents. Often a sugar solution or another coating material is included. Blocking agents include bovine serum albumin (BSA), methylated BSA, casein, nonfat dry milk. Stabilizing agents are readily available and well known in the art, and may be used, for example, to stabilize labeled reagents. In frequent embodiments, employment of the selected blocking and stabilizing agents together with labeled reagent in the labeling zone followed by, or in conjunction with, the drying of the blocking and stabilizing agents (e.g., a freeze-drying or forced air heat drying process) is utilized to attain improved performance of the device.

The label zone ("label zone" is intended to encompass any area of the device including a mobilizable labeled reagent) generally contains a labeled reagent, often comprising one or more labeled reagents. In many of the presently contemplated embodiments, multiple types of labeled reagents are incorporated in the label zone such that they permeate together with a fluid sample contacted with the device. These multiple types of labeled reagents can be analyte-specific or control reagents and may have different detectable characteristics (e.g., different colors) such that one labeled reagent can be differentiated from another labeled reagent if utilized in the same device. As the labeled reagents are frequently bound to a specific analyte of interest subsequent to fluid sample flow through the label zone, differential detection of labeled reagents having different specificities (including analyte specific and control labeled reagents) may be a desirable attribute. However, frequently, the ability to differentially detect the labeled reagents having different specificities based on the label component alone is often unnecessary when both test and control zones are incorporated in the device, which allow for the accumulation of labeled reagent in designated zones.

The label zone containing labeled reagents is present in a flow path of the device and may also include a coating. Often, two or more label zones are present on a device and often the two or more label zones contain different labeled reagents. A label zone may, for example, be positioned in a sample pad, a sample zone, a test strip, a channel or in a portion of the device positioned upstream of a channel.

In certain embodiments, a nonparticulate labeling scheme is provided. In these devices, a label which is a dyed antibody-enzyme complex is utilized. This dyed antibody-enzyme complex can be prepared by polymerizing an antibody-enzyme conjugate in the presence of enzyme substrate and surfactant. See, e.g., WO 9401775. Generally, the label zone contains detectable moieties comprising enzyme-antibody conjugate, particulate labeled reagents, or dye labeled reagents, metal sol labeled reagents, etc., or moieties which may or may not be visible, but which can be detected if accumulated in the test and/or control zones. The detectable moieties can be dyes or dyed polymers which are visible when present in sufficient quantity, or can be, and are preferred to be particles such as dyed or colored latex beads, liposomes, metallic or non-metallic colloids, organic, inorganic or dye solutions, dyed or colored cells or organisms, cellulose nanoparticles, red blood cells and the like. The detectable moieties used in the assay provide the means for detection of the nature of and/or quantity of result, and accordingly, their localization in the test zones may be a function of the analyte in the sample. In general, this can be accomplished by coupling the detectable moieties to a ligand which binds specifically to an analyte of interest, or which competes with an analyte of interest for the means which permit the restraint of an analyte of interest positioned in the test zone(s). In the first approach, the detectable moieties are coupled to a specific binding partner which binds the analyte specifically. For example, if the analyte is an antigen, an antibody specific for this antigen may be used; immunologically reactive fragments of the antibody, such as F(ab')2, Fab or Fab' can also be used. These ligands coupled to the detectable moieties then bind to an analyte of interest if present in the sample as the sample passes through the labeling zone and are carried into the test region by the fluid flow through the device. When the labeled analyte reaches the capture zone, it is restrained by a restraint reagent which is analyte-specific, label/detectable moiety-specific, or ligand-specific, such as an antibody or another member of a specific binding pair. In the second approach, the conjugate or particulate moieties are coupled to a ligand which is competitive with analyte for an analyte-specific restraint reagent in a test zone. Both the analyte from the sample and the competitor bound to the detectable moieties progress with the flow of the fluid sample to the test region. Both analyte and its competitor then react with the analyte-specific restraint reagent positioned in a test zone. The unlabeled analyte thus is able to reduce the quantity of competitor-conjugated detectable moieties which are retained in the test zone. This reduction in retention of the detectable moieties becomes a measure of the analyte in the sample.

The labeling zone of the present devices also often includes control-type reagents. These often labeled control reagents often comprise detectable moieties that will not become restrained in the test zones and that are carried through to the test region and control zone(s) by fluid sample flow through the device. In a frequent embodiment, these detectable moieties are coupled to a member of a specific binding pair to form a control conjugate that can then be restrained in a separate control zone of the test region by a corresponding member of the specific binding pair to verify that the flow of liquid is as expected. The visible moieties used in the labeled control reagents may be the same or different color, or of the same or different type, as those used in the analyte of interest specific labeled reagents. If different colors are used, ease of observing the results may be enhanced. Generally, as used herein, the labeled control reagents are also referred to herein together with analyte specific labeled reagents or labeled test reagents as "labeled reagent(s)."

Unlike traditional lateral flow devices, the test region/zone is generally not comprised of nitrocellulose, nylon, or hydrophilic polyvinylidene difluoride (PVDF). As indicated, nitrocellulose is nor flushable due at least to its toxicity, nor is it water dispersible. Rather, most frequently, the test zone is comprised of a water dispersible or soluble material such as WDMSM. Frequently, the term "test region" or "test zone" is utilized herein to refer to a region in/on a device that comprises at least the test and control lines/areas. To provide non-bibulous flow, these materials may be treated with agents such as blocking agents that can block the forces which account for the bibulous nature of bibulous membranes. Suitable blocking agents include bovine serum albumin, methylated bovine serum albumin, whole animal serum, casein, and non-fat dry milk, as well as a number of detergents and polymers, e.g., PEG, PVA and the like. Preferably the interfering sites on the untreated bibulous membranes are completely blocked with the blocking agent to permit non-bibulous flow there through. The present disclosure envisages a test device with multiple test and control areas.

The test zone often, though not always, includes a control area that is useful to verify that the sample flow is as expected. Each of the control areas comprises a spatially distinct region that often includes an immobilized member of a specific binding pair which reacts with a labeled control reagent. In an occasional embodiment, the procedural control area contains an authentic sample of the analyte of interest, or a fragment thereof. In this embodiment, one type of labeled reagent can be utilized, wherein fluid sample transports the labeled reagent to the test and control areas; and the labeled reagent not bound to an analyte of interest will then bind to the authentic sample of the analyte of interest positioned in the control area. In another embodiment, the control line contains antibody that is specific for, or otherwise provides for the immobilization of, the labeled reagent. In operation, a labeled reagent is restrained in each of the one or more control areas, even when any or all the analytes of interest are absent from the test sample.

In a less occasional embodiment, a labeled control reagent is introduced into the fluid sample flow, upstream from the control area. For example, the labeled control reagent may be added to the fluid sample before the sample is applied to the assay device. In frequent embodiments, the labeled control reagent may be diffusively bound in the sample receiving zone, but is preferably diffusively bound in the label zone.

Exemplary functions of the labeled control reagents and areas include, for example, the confirmation that the liquid flow of the sample effectively solubilized and mobilized the labeled reagents deposited in the label zone, that a sufficient amount of liquid traveled correctly through the sample receiving zone, label zone, and the test and control areas, such that a sufficient amount of analyte could react with the corresponding specific label in the label zone, migrate onto the test region comprising the test and control areas, cross the test zone(s) in an amount such that the accumulation of the labeled analyte would produce a visible or otherwise readable signal in the case of a positive test result in the test zone(s). Moreover, an additional function of the control areas may be to act as reference zones which allow the user to identify the test results which are displayed as readable zones.

Since the devices of the present invention may incorporate one or more control areas, the labeled control reagent and their corresponding control areas are preferably developed such that each control area will become visible with a desired intensity for all control zones after fluid sample is contacted with the device, regardless of the presence or absence of one or more analytes of interest.

In one embodiment, a single labeled control reagent will be captured by each of the control zones on the test strip. Frequently, such a labeled control reagent will be deposited onto or in the label zone in an amount exceeding the capacity of the total binding capacity of the combined control zones if multiple control areas are present. Accordingly, the amount of capture reagent specific for the control label can be deposited in an amount that allows for the generation of desired signal intensity in the one or more control areas, and allows each of the control areas to restrain a desired amount of labeled control reagent. At the completion of an assay, each of the control areas preferably provide a desired and/or pre-designed signal (in intensity and form). Examples of contemplated pre-designed signals include signals of equal intensities in each control zone, or following a desired pattern of increasing, decreasing or other signal intensity in the control areas.

In another embodiment, each control area will be specific for a unique control reagent. In this embodiment, the label zone may include multiple and different labeled control reagents, equaling the number of control areas in the assay, or a related variation. Wherein each of the labeled control reagents may become restrained in one or more pre-determined and specific control area(s). These labeled control reagents can provide the same detectable signal (e.g., be of the same color) or provide distinguishable detectable signals (e.g., have different colored labels or other detection systems) upon accumulation in the control area(s).

In yet another embodiment, the control areas may include a combination of the two types of control areas described in the two previous embodiments, specifically, one or more control areas are able to restrain or bind a single type of labeled control reagent, and other control areas on the same test strip will be capable of binding one or several other specific labeled control reagents.

In one embodiment, the labeled control reagent comprises a detectable moiety coupled to a member of a specific binding pair. Typically, a labeled control reagent is chosen to be different from the reagent that is recognized by the means which are capable of restraining an analyte of interest in the test zone. Further, the labeled control reagent is generally not specific for the analyte. In a frequent embodiment, the labeled control reagent is capable of binding the corresponding member of a specific binding pair or control capture partner that is immobilized on or in the control area. Thus the labeled control reagent is directly restrained in the control area.

In another embodiment, the detectable moiety which forms the label component of the labeled control reagent is the same detectable moiety as that which is utilized as the label component of the analyte of interest labeled test reagent. In a frequent embodiment, the label component of the labeled control reagent is different from the label component of the labeled test reagent, so that results of the assay are easily determined. In another frequent embodiment, the control label and the test label include colored beads, e.g., colored latex, gold particles or colloids, cellulose nanobeads. Also frequently, the control and test beads comprise different colors or may each be of a different type of label (e.g., colored latex, gold colloids, cellulose nanobeads). In one embodiment, colloidal gold is provided as a control (e.g., any protein or Ab) label and latex beads are provided as a test (e.g., hCG) label. Cellulose nanobeads may be substituted for either or both in certain embodiments.

In a further embodiment, the labeled control reagent includes streptavidin, avidin or biotin and the control capture partner includes the corresponding member of such specific binding pairs, which readily and specifically bind with one another. In one example, the labeled control reagent includes biotin, and the control capture partner includes streptavidin. The artisan will appreciate that other members of specific binding pairs can alternatively be used, including, for example, antigen/antibody reactions unrelated to analyte.

The use of a control area is helpful, for example, in that appearance of a signal in the control zone indicates the time at which the test result can be read, even for a negative result. Thus, when the expected signal appears in the control line, the presence or absence of a signal in a test zone can be noted.

In still further embodiment, a control area comprising a mark that becomes visible in the test region when the test region is in a moist state is utilized. In occasional embodiments, one or more control areas of this type are utilized. In another embodiment, a combination of control areas of the type utilizing labeled control reagents and control area and of the type that display the control area when in a moist state can be used. This allows a simple way to formulate control areas while allowing to use a reagent-based control area to ascertain that the re-solubilization and mobilization of the reagents in the label pad process has been effective, and that the specific reactions took place as expected, all along the path defined by the sample receiving zone, label pad, test strip and absorbent zone. The present embodiment includes the use of one or more control zones that become visible when the test region is in the moist state for each of the control areas of an assay, except the control area on the distal or downstream end of the test strip.

As indicated above, labeled test reagents are further provided which frequently comprise a test label coupled to a member of a specific binding pair that is capable of specifically binding an analyte of interest. Thus, in general, multiple labeled test reagents are positioned in the label zone, each of which is specific for a predetermined analyte of interest.

Test zones of the present description include means that permit the restraint of an analyte of interest. Frequently, test zones of the present description include a ligand that is capable of specifically binding to an analyte of interest. Alternatively, test zones of the present description include a ligand that is capable of specifically binding the labeled reagent bound to an analyte of interest. In practice, a labeled test reagent binds an analyte of interest present in a fluid sample after contact of the sample with a representative device and flow of the fluid sample into and through the label zone. Thereafter, the fluid sample containing the labeled analyte progresses to a test zone and becomes restrained in the test zone. The accumulation of labeled analyte in the test zone produces a detectable signal. Frequently, devices of the present disclosure incorporate one or more test zones, each of which is capable of restraining different analytes, if present, in a fluid sample. Thus, in representative embodiments two, three, four, five or more (labeled) analytes of interest can be restrained in a single or different test zones, and thereby detected, in a single device.

The present devices optionally further comprises an absorbent zone that acts to absorb excess sample after the sample migrates through the test region. The absorbent zone, when present, lies in fluid flow contact with the test region. This fluid flow contact can comprise a contiguous, overlapping, abutting or interlaced type of contact. In an occasional embodiment, a control region (end of assay indicator) is provided in the absorbent zone to indicate when the assay is complete. In this embodiment, specialized reagents are utilized, such as pH sensitive reagents (such as bromocresol green), to indicate when the fluid sample has permeated past all of the test and control zones. Alternatively, the end of assay control region may be effected by applying a line of soluble ink on the test region after all of the test and control zones, and at the interface with the absorbent zone. In general, the liquid front moving through the capture zone will solubilize the ink and transfer it into the absorbent. The resulting color change will be seen in an observation window above the absorbent zone, signifying end of assay. Thus, these types of control areas are not specific for a particular analyte. Generally, the absorbent zone will consist of an absorbent material such as filter paper, a glass fiber filter, or the like.

In an occasional embodiment, the fluid sample must be processed or treated prior to contact with the device to ensure accurate detection of at least one of the multiple analytes of interest. In this embodiment, a reagent, such as an extraction solution, may be used to prepare the sample. Alternatively, reagents can be added to the test device after initial contact with the fluid sample. For example, the sample is introduced to the device, and thereafter a reagent, such as a developer solution, is added to complete the assay.

The present devices tackle the competing issues of rapid time to sample answer, high analyte sensitivity, and high results accuracy. As part of meeting these issues a variety of innovations described here have been developed. In addition, reagent choice and reagent concentrations may be optimized to meeting one or more of these competing issues. For example, it has been found that the fluid flow rates through the matrix materials contemplated here are quite high, but the surface area of the underlying nonwoven structure is less dense than typical axial flow materials such as nitrocellulose. Given the rapid sample flow rate, obtaining rapid release of reagents deposited on the matrix is often important to ensure a maximal opportunity for the reagent to interact with and bind (e.g., in am immunoassay) an analyte in the sample. Moreover, since the underlying nonwoven structure is less dense, the concentration of reagent bound to the structure is lower compared with traditional devices. This lower concentration affects test and control capture lines/reagents and the resulting signals. Therefore, reagents and concentrations are selected to enhance release of (conjugate) reagents that will interact with a desired analyte, reagents and concentrations of capture reagents are selected to bind well with the underlying nonwoven structure, and reagents and concentrations of label reagents are selected to provide a strong or amplified visual signal of test results.

In certain embodiments, the capture reagents for the test line are adjusted in pH to make them more acidic than is typical (e.g., low pH shock), which has been shown to enhance binding of the reagents to the underlying matrix structure. Treatment of the capture reagents with salt (e.g., sodium acetate) may also be employed to enhance binding. Specialty cross-linking (e.g., paper cross-linkers or another treatment or reagent to aid the adherence to the matrix structure) may also be employed.

On one exemplary embodiment for a pregnancy (hCG) test, certain of the reagents comprise the following:
Polyclonal test line
    Control Line:goat anti-rabbit (GAR) Control Line
        Corresponding control Conjugate-rbIgG Control conjugate (Rabbit IgG)
    Test line: Goat anti Alpha hCG, ABACG-0500 polyclonal antibody (Arista)
        Corresponding Test conjugate-Clone 2 anti-BhCG conjugate (colloidal gold) (Arista)
Monoclonal test line
    Control Line:goat anti-rabbit (GAR) Control Line
        Corresponding control Conjugate-rbIgG Control conjugate (Rabbit IgG)
    Test line: clone 1 monoclonal anti-ahCG (Arista)
        Corresponding Test conjugate-Clone 2 anti-BhCG conjugate (colloidal gold) (BBI Conjugate or Arista)
Latex microparticles may be employed in place of gold for the test line indicator. As the latex particles are larger, these particles provide the opportunity to incorporate additional antibody copies and amplify resulting signals, thus improving sensitivity
Conjugates
    15-25% sugars to aid encapsulate conjugate on web and release with solution (e.g., 10% sucrose, 5% trehalose)
Sample receiving zone Buffers/reagents:
    BSA (1-2%)
    Tris buffer/pH 8.0 (Tris/8.0) with low concentrations (0.1%) of Tween-20 and NP40 surfactants, serum, NP40, tween20
    Borate A variety of coatings are contemplated according to methods and devices described herein. Coatings generally may refer (1) to reagents used to deposit reagents to ensure their ready solubility in response to contact with a sample or to adhere them to a matrix material; or (2) to treat a material such as a matrix material to adjust its ability to, for example, absorb or repel water or sample. In this section, coatings related to the deposition of reagents is discussed.

FIG. 6, for example, details some of the types of coatings that are contemplated and certain of their uses. As can be seen, wet-strength resins, polyvinyl alcohol (PVA), Polyamide-epichlorohydrin (PAE), propylene glycol alginate (PGA), collagen, gelatin, dissolvable films, polyethylene glycol (PEG), water soluble silicone, silica and non-silica sol gels, hydrogels (e.g., PVA and/or PGA hydrogels), Natural, water-soluble and water-dispersible or soluble waxes, among others including a variety of additional water dispersible or soluble coatings that do not adversely affect the operability of the reagents such as antibody-based reagents contemplated herein. Other water soluble polymers include, for example, those discussed in U.S. Pat. Nos. 4,256,724, 5,399,500, 7,425,292, 7,666,337, 7,910,641, 8,282,954, 8,383,198; Water Soluble Polymers, available at «snf.com.au/downloads/Water_Soluble Polymers_E.pdf».

Most frequently, the coating is naturally soluble or dispersible or soluble in water (or another fluid such as a fluid sample, including urine, blood, serum, bile, CNF fluid, lymph, saliva, gastric fluids, etc.), which means that upon contact with the fluid, the polymer material becomes a homogeneous liquid or solution. For ease of reference these coatings are referred to as water soluble, but included in this meaning is intended solubility in any of the variety of fluid sample types contemplated herein. One advantage of using a coating that is naturally soluble in water rather than a non-water soluble coating that is not water-soluble is that the reagent such as a receptor, ligand, and/or label is rapidly released from the water-soluble coating after contact with an aqueous sample, which then becomes available for a binding reaction. Another advantage is that the water-soluble coating is easily applied to a support or non-synthetic matrix material using standard methods and agents. See, e.g., Kim & Herr, Biomicrofluidics 7(4):041501 (July 2013); Qian et al., Clin. Chem. 46(9):1456-1463 (2000); Reis et al., Mat. Res. 9(2):185-191 (2006).

Coating materials naturally soluble in water that are useful in the present devices and methods are preferably soluble to the extent that a layer of the coating about 0.25 μm-1.0 mm in thickness will dissolve in less than about 60 minutes (preferably less than 10 minutes, or less than 5 minutes, or less than 3 minutes, less than 2 minutes, or less than 1 minute) when contacted with water at a pre-determined temperature or temperature range such as human body temperature. The most frequent coatings dissolve in less than 60 seconds when contacted with water (e.g., urine) at or around body temperature. Examples of polymeric materials that are useful in the present invention include hydroxypropyl cellulose, hydroxyethyl cellulose, carboxymethyl cellulose, and carboxypropyl cellulose. Other useful polymeric materials include unhardened gelatin, poly (vinyl-alcohol), poly(vinylpyrrolidone), poly(acrylamide) or any mixtures or copolymers. The coating can be applied as a layer by known means.

In certain embodiments, when the first and second reagent zones of the invention are contained in a single layer of an analytical element, one method of preparing that layer is to prepare a spreading layer (e.g., U.S. Pat. No. 4,258,001), having a biologically active material such as an antibody immobilized on the surfaces of particles. A solution of a water-soluble polymeric material and a second biologically active material such as a labeled antigen reactive with the antibody is then coated on the first layer. This coating step is performed, for example, such that the water-soluble polymer spreads into the spreading layer during the coating operation, coating the polymer particles in a way such that the two biologically active materials do not react.

A coating propylene glycol alginate, sucrose, PVG, PEG, or another material discussed herein, for example, is often in the range of about 10% to about 50% by dry weight of the coating composition. The coating materials contemplated herein often have a wide variance in viscosity. An example of a high viscosity coating material is a 2% aqueous solution of the material having a viscosity in the range of 700 to 1800 mPa·s at 25° C. An example of a low viscosity coating material is a 2% aqueous solution of the material having a viscosity in the range of 20-30 mPa·s at 25° C. In general, high viscosity coatings are employed in lower amounts versus that employed for low viscosity coatings.

In certain embodiments, multiple water dispersible or soluble coatings or coating materials are used, optionally in a layered format, to form a microfluidic channel (or multiple channels) in a coating layer or within multiple coatings. In such embodiments, a microfluidic-styled device may be created permitting or facilitating the passage of a sample (or portion thereof) and reagents through the microfluidic channel(s). Any of a variety of techniques known in the art are contemplated for channel formation. See, e.g., U.S. Pat. Nos. 8,367,019, 8,101,139, 8,920,879; U.S. Application Pub. Nos. 20060001039, 20120208265, 20140106454, each of which is incorporated herein by reference. The microfluidic channel can optionally form a specific zone/portion, or multiple zones/portions, of the device. For example, the sample receiving zone, label zone, test zone, and/or absorbent zone. In certain embodiments, when microfluidic channels are employed, that the rate of dispersion or dissolution is decreased such that the coating or coatings used in the device disperse or dissolve over a prolonged period of time beginning after the completion of an assay using the device. Preferably, such materials dissolve or are dispersed within water within one month or one week of contact with a sample, more preferably within one day. In such embodiments, water dispersible or soluble coating materials are often selected to provide for longer dispersion or dissolution times (e.g., less than about 3 months, or less than about 6 or 9 months).

In certain embodiments, an excipient, e.g., an acid, a base, etc., is contacted, provided, or utilized to enhance or speed dissolution or dispersion of materials of the devices contemplated herein. In certain embodiments, at least one coating of the coatings contemplated herein comprises an enteric coating.

The sample receiving zone, test strip, and/or absorbent zone may be embossed to enhance liquid capture and liquid flow management. For example, an embossing patterns may be provided to guide liquid into less dense areas from more dense areas or to create one or more channels to siphon or direct liquid from one portion of the device to another. In certain embodiments, embossing may be used to interrupt, slow, change, or redirect liquid wicking within the matrix material of the device or one of its components. Embossing may also be utilized to increase or alter the surface area of the matrix material that is available for liquid absorption.

To withstand the rigors of device use, and/or to maintain device rigidity, during and after sample application, the matrix comprising the fluid flow path may be incorporated in a housing, covering, or other support (often referred to herein as a "support layer" or "housing"). Importantly, this support or housing must be water-dispersible or biodegradable. Most often, the housing or support is flushable and meets flushability guidelines noted herein. While most frequently the housing or support is comprised of the same matrix material as the fluid flow path, it may be comprised of a different matrix material if the disposal guidelines are met. The inventors have found that matrix materials discussed herein often become malleable or flexible when exposed to a liquid sample. While this is a desirable quality in a water dispersible material, integrity of the flow path should be maintained for a duration sufficient to complete an assay such as a pregnancy test. A housing or support, therefore, is often provided such that it supports the fluid flow path during an assay and for a time period after sample contact. The housing may in certain embodiments be adapted such that it does not contact the sample, even after it is contacted with the device. In such embodiments, the housing or support may be comprised of the same basic type of matrix material, which may be treated or untreated (e.g., with a hydrophobic substance or other water-soluble coating material), and may be embossed or non-embossed.

The support is often adapted to encompass, encase, or envelop the test strip, including if present, the sample zone, label zone, test zone, and/or absorbent zone. The support may also be referred to herein as a housing.

In often included embodiments, the housing or support is comprised of a matrix material that is treated with a reagent such as a hydrophobic solution, e.g., a solution including a hydrophobic nanoparticle, for example, as taught in commonly owned U.S. Provisional Patent Application Ser. No. 62/362,813, filed Jul. 15, 2016 (the teachings of which are hereby incorporated by reference). The support layer may be comprised of or include a water-soluble film (e.g., AQUA-FILM®, MonoSol, LLC, Portage, Ind.), water-soluble polymer (e.g., polylactic acid and many others known in the art), a wax (e.g., soy wax), or other treatment, coextrusion, or coating. Often, when a water-soluble film or water-soluble polymer is selected, it is soluble at normal environmental temperatures, including typical temperature average or low temperature ranges in sewage or waste treatment systems.

The support layer may also provide protective qualities to the device. For example, the support layer may be formed as a covering that covers the test strip and/or other components of the device from the outside environment. Such protection will often enhance shelf life and/or ease the functional portability of the device.

The support layer may also comprise removable portions located over, covering, or surrounding the test region and/or sample receiving zone to provide enhanced protection of the device from contamination prior to, or during, use. Such removable portions may comprise an additional portion of matrix material (often treated to maintain some hydrophobicity) adhered to the support or otherwise adjacent the test region and/or sample receiving zone. In certain embodiments, the removable portion comprises a portion of the support (or material adhered thereto) that is tearable to remove it prior to or after use. Including indentations surrounding at least a portion of the portion to be removed, and optionally including a tab or other portion to grasp for tearing.

Though not wishing to be bound by any particular theory of operation, the inclusion of a support layer that closely parallels the test strip may affect fluid dynamics and fluid flow through the test strip. For example, the support may be laminated to the test strip, the test strip can be positioned in contact with the support, sandwiched between portions or the support, or other configuration. When the support layer affects fluid flow rates through the test strip, the inclusion of a support layer that contacts the test strip is provided to increase or decrease flow rates through portions of, or the entire, test strip. Often the support layer is provided with vented portions to permit entrained air to escape the matrix as sample fluid flows through the matrix material.

Often, the support layer is provided to ensure that the test strip is held in a pre-determined orientation for the duration of an assay. For example, the support layer is provided such that the test strip is held in a predetermined horizontal, vertical, or angled orientation during an assay. Often the support provides this ability due to its structural rigidity for the duration of an assay.

It has also been discovered that the inclusion of a reinforced portion in the device around the area of the sample receiving zone is often beneficial. In particular, the sample receiving zone area of the device generally will see the largest fluid volume contact, and will also be the portion of the device contacted for the longest period of time as an assay is conducted. This larger volume and longer time may affect the integrity of the device in this region such that it may prematurely begin to soften, bend, dissolve, or break apart before the completion of an assay. Therefore, a reinforcement comprising or comprised in the sample treatment area (the area around the sample receiving zone) is often provided. Treatments such as the inclusion of a layer of soy wax, Progel (M1, available from LD Davis Industries), a water soluble polymer, or the like, behind the sample receiving zone may be utilized. Additional layers of support material or matrix material may be utilized. A hydrophobic coating (e.g., including a hydrophobic nanoparticle solution) may be utilized. As such, the "reinforced" aspect of this portion is provided relative to the fluid volume introduced to the device and often it does not comprise a separate physical component, but rather a surface treatment, matrix treatment, or coextrusion.

The support is provided most frequently in a physical orientation, and with corresponding dimensions, that permit it to pass through a toilet bowl trap in a single flush. For example, as depicted in FIG. 17C, aspects W and W' refer to the width of the device that is often adapted in such a manner. While such dimensions are often included, they are not required. For example, the device may provided such that the matrix material softens such that it becomes flexible in a matter that it will clear a toilet bowl trap in a single flush. Again, with reference to the device depicted in FIG. 17C, the outer extremities (or shoulders) of one or both of aspects W and W' (i.e., outside the raised portion (21)), may soften more rapidly than raised portion (21) permitting them to fold. Alternatively, raised portion (21) may soften quicker than the outer extremities of one or both of aspects W and W', permitting the shoulders to fold together with the raised portion (21) as the axis.

Methods of manufacturing exemplary devices are also contemplated herein, as noted elsewhere. A single manufacturing line is used in exemplary embodiments to prepare such devices. Such efficiency in manufacturing is provided since the device is often comprised of a single matrix type, including various matrix surface treatments and adaptations. One exemplary process involves certain of the following processes:

A single roll of matrix material is provided, rolled out and split into multiple webs of matrix material. From this single roll of matrix material, an entire device as contemplated herein may be made from the multiple webs. The splitting of the single roll of matrix material may occur as part of a continuous process of manufacture, or it may occur in one step separate from the device manufacturing step. In any event, multiple webs of the same matrix material may be treated (with reagents) differently, laminated, punched, slit, etc. and combined in a process that produces the final devices described herein.

A hydrophobic solution (as contemplated herein) is applied to one or more of the multiple webs of the matrix, e.g., via dip and squeeze, spray, printing, vapor deposition, or another method (i.e., lamination). As such, one or more of the multiple webs that are divided in the prior step may be treated with a hydrophobic solution, and others remain untreated.

The matrix is dried, if necessary, e.g., using an elevated temperature, dry air, drying cans, microwave technology, or another method.

Rotary Die conversion of coated, laminated roll. For example, one or more components of the support are punched out from the laminated/hydrophobically treated matrix material using a rotary steel die.

Reagents are applied to the matrix using, for example, one or more of the following methods or techniques.
  BioDot systems
  Gravure roll striping
  Traditional striping techniques
  For conjugate application, the following techniques are often employed. These permit the placement of single or multiple types of conjugate, optionally in different locations on the device:
    Spray
    Soak
    Other
  For sample zone buffer application, the following techniques are often employed. These permit the placement of buffers, optionally in different locations on the device:
    Spray
    Soak
    Stripe When the devices are comprised of multiple components (even if they are comprised of the same material or matrix type), the various components are often automatically assembled, for example by employing one or more of the following techniques:
  Mechanical assembly requiring no adhesive
    Press fits, ultrasonic welding, embossing, etc.
    Stitching/Sewing
      PVA watersoluble thread
      Cotton thread
      other
  Pressure sensitive adhesives may also be employed, which must be water soluble. These often are provided on release liners for roll-to-roll application
  Liquid/Spray adhesives are generally also water soluble. Liquid starch is one exemplary adhesive type.

The chemistry of the device is often protected using a shield or window where it is intended to produce a visible result in use. Gelatine, for example, provides a clear window that does not wrinkle in use, but still completely dissolves. Gelatine is available from PerfectaGel (e.g., Silver 170+ Bloom, 100% Grade A Porcine Gelatin, 0.006 inch sheet thickness) MonoSol films and the like may also be employed.

The device may be embossed to provide texture and form to the support or other components, which is typically provided by pressure embossing though heated embossing may also be employed. The device, including portions thereof such as the support may be punched or slit to enhance wettability, sinkability, and/or flushability of the device, including facilitating water dispersion of the matrix material.

Printing—the matrix material, including support material, may have printed portions that provide various information-related, iconography, instructions, aesthetic, branding, or functional aspects or purposes. In certain embodiments, the test and/or control lines include a printed ink or dye (e.g., blue, green, pink, etc.) to locate the position of these lines. Flexographic or screen printing may be employed for such printing (e.g., RUCO brand Series T200; Colorcon brand No Tox Medical Device Vinyl Inks). This printed portion of the test and/or control lines provides another control and generally does not affect the results of the assay, but rather enhanced the readability of the results of the assay.

An embodiment of the present teachings can include an immunoassay device or diagnostic test device that may be manufactured using a continuous manufacturing process or conversion-based line to form the device. The manufacturing process may overlay reagent materials onto a matrix using one or more printing or coating processes. This eliminates the need for final lamination of all separate components because the process inherently integrates components. Manufacturing techniques may be carried out in one machine, or multiple machines on an automated or semi-automated line. This process can also be simulated manually, for example, for a small number of units. The immunoassay device or diagnostic test device may be any axial flow device used for detecting a chemical using a reagent.

FIG. 1 depicts an embodiment of an immunoassay device that may be formed using an embodiment of the present teachings. It will be apparent to one of ordinary skill in the art that the structure depicted in FIG. 1 represents a generalized schematic illustration and that other structures or elements may be added or existing structures or elements may be removed or modified.

FIG. 1 depicts an embodiment including one or more matrix layers that together form a matrix, one or more channel layers (i.e., channels, reagent channels) formed on or within the matrix, and one or more reagents formed within the one or more channels and on or within the matrix.

The one or more matrix layers may be non-woven layers manufactured, for example, from paper, cellulose pulp, hydrogen-bonded cellulose, airlaid non-woven, another suitable water dispersible and/or water soluble material, or a combination of two or more of these. In an embodiment, the one or more matrix layers may be a HYDRASPUN® material, available from Suominen Corporation, or a combination of HYDRASPUN® with one or more of the foregoing materials.

The one or more channels that contain the one or more reagents may be formed on the matrix using various materials such as paper, cellulose, or another suitable material to form channel walls or channel borders. The channels may be formed by dispensing a suitable material onto the matrix directly in a pattern, for example, using a printing process such as ink-jet printing or other printing of the channels. The channels may be formed by applying a pre-patterned layer or coating having channel openings over the matrix layer. In an embodiment, the channels may be formed from the same material as the matrix, or a different material. In another embodiment, the one or more channels may be formed by embossing, indenting, or otherwise deforming the matrix such that channel walls are formed from the matrix itself. Channels may be formed using any suitable technique such as embossing the matrix with a wheel or blade, stamping the matrix with a stamp or die, removing a portion of the matrix using a blade or a laser, or another suitable technique.

The reagents may be formed from any known reagent material that is suitable for the immunoassay that is to be performed using the diagnostic test device. In an embodiment, the reagent may be embedded or impregnated into another material, such as a cellulosic material or another water-soluble and/or water-dispersible material, and then dispensed over, on, or within a matrix. Further, the reagents may be physically separated from one or more matrix layers by one or more layers or coatings, such as a non-nitrocellulose coating. In an embodiment, the immunoassay can be designed to test for various analytes. For example, in one embodiment the immunoassay could be designed to test for the hormone hCG which would allow the device to return a result with respect to whether the user is pregnant. However, the device can be designed to test for any number of analytes including, but not limited to, hCG-H and various drugs (such as cocaine, THC, or amphetamines), glucose, ketones, luteinizing hormone, or hemoglobin. Depending on the analyte chosen, the device can be designed to test for various conditions, diseases, or other information including the presence of sexually transmitted diseases, diabetes, pregnancy, kidney disease, or cancers. The reagents may be water dispersible and/or water soluble. These devices can be used in a variety of industries, including medical, food safety, and environmental control. Additionally, other water-dispersible and/or water-soluble components may be added for improved function, such as dissolvable circuits.

Figure 2:
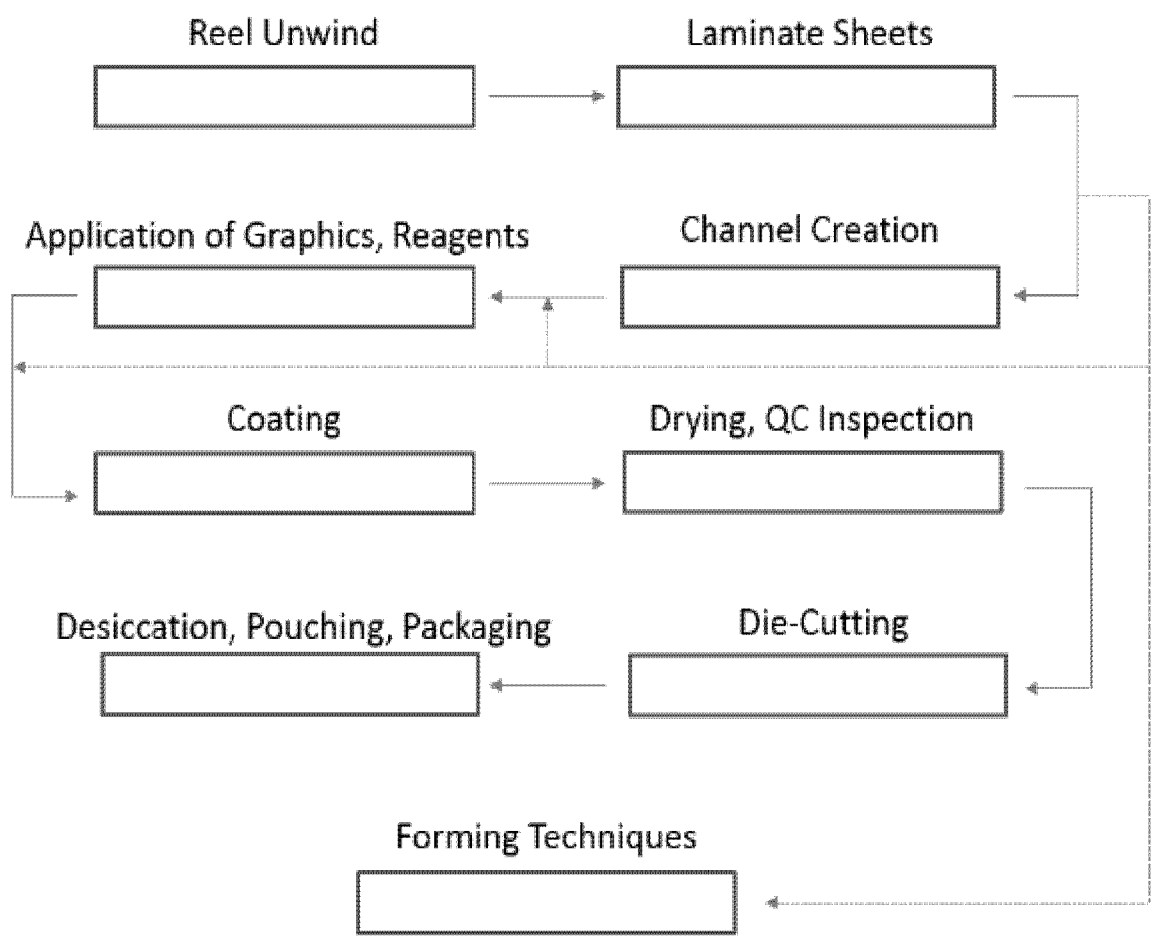
FIG. 2 is a flow chart depicting an embodiment of a method for forming a diagnostic test device in accordance with an embodiment of the present teachings.

FIG. 2 is a flow chart depicting a generalized manufacturing process in accordance with an embodiment of the present teachings to form the structure of FIG. 1 or another embodiment. It will be appreciated that while the process is described and depicted as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or embodiments of the present teachings. It will be appreciated that processing stages can be added or illustrated processing stages can be removed or modified.

As depicted in FIG. 2, the matrix may be stored as on one or more matrix layer, for example, on one or more rolls or reels, as one or more individual matrix sheets, or the matrix may be stored in another suitable form. Any initial processing is performed to prepare the matrix for device manufacture, for example, calendaring to control surface topography or moisture content.

A single matrix layer may be used as the matrix, for example, if a single layer is sufficient. In another embodiment, or two or more matrix layers may be laminated together as depicted in the flow chart of FIG. 2 to create a web. Lamination may be performed using any suitable process, for example, thermal (heat) bonding, ultrasonic bonding, binding using a suitable water dispersible and/or water soluble adhesive agent such as polyvinyl alcohol (PVOH or PVA), polyethylene glycol (PEG), or another water soluble and/or water dispersible material. Lamination may be performed at a diagnostic test device manufacturing facility or by a supplier prior to receipt by the manufacturing facility.

Subsequently, one or more channels that will direct liquid flow may be formed on or within the matrix, for example, embossing of the matrix, ink-jet printing or other printing of the channels using a cellulose, PVOH, or other suitable channel print material, and/or laser cutting the channels into the matrix. In another embodiment, the channels may be formed prior to laminating the matrix web using, for example, a patterned top matrix layer having one or more channel openings therein.

Next, one or more reagents, antibodies, diagnostic chemistries, etc. (hereinafter, collectively, "reagents") required to run the diagnostic are dispensed onto to the matrix as at least one of a liquid, solid, or gel form, or a combination of two or more of these forms, using functions and processing native to both an axial flow and paper product manufacturing processes. The reagent dispensing technique may include contact application onto the matrix, for example, using a stamping, screen print, or contact tip dispensing process. Suitable contact tip dispensers include, for example, those available from BioDot (Irvine, Calif.), Imagene Technology, Inc. (Hanover, N.H.), and ZETA Corporation (Korea). The reagent application process may further include a non-contact dispensing process using, for example, non-contact pump-driven solenoid dispensers, airbrush dispensers, ink-jet printing, spray coating, or another suitable process. The same dispensing process, or a different process, may be used to dispense indicia such as graphics or text to the matrix or another surface, for example, words, symbols, instructions, lot numbers, part numbers, etc., either in parallel or sequence with the application of the reagent. The indicia may include a quick response code (i.e., QR code®), bar code, or another code that may be, for example, read by a cell phone, an optical or electronic scanner, or another device. Any indicia may be printed using any ink or pigment compatible with the device and the application process. As discussed above, in an embodiment, the reagent may be embedded or impregnated into another material, such as a cellulosic material or another water-soluble and/or water-dispersible material, and then dispensed over, on, or within a matrix.

After reagent application, an optional coating may be applied to the reagent and/or indicia, for example, to prevent contamination or increase chemical stability of the one or more reagents. The optional coating may include a non-nitrocellulose coating. Coatings contemplated include temporary wet-strength resins (e.g., glyoxalated polyacrylamide, sof-strength®, and others), PVOH (e.g., Elvanol, SOLUBLON® water soluble and/or water dispersible PVA film, Poval, PVA/PGA), MonololRX, dissolvable films available from Adhesives Research, PEGs such as CARBO-WAX™ PEGs, sucrose, collagen, gelatin, organically modified silica or another sol-gel, natural water dispersible and/or water soluble waxes such as soybean wax, water-dispersible and/or water-soluble silicones, or another suitable coating.

Subsequently, the matrix may be sent to a curing device such as a drying oven.

At this point, or during any other point in the manufacturing process, quality control and/or inspection may be performed on the in-process device or the completed device to ensure product quality and consistency.

Next, the matrix may be sectioned into a plurality of individual matrix sections using, for example, cutting with a rotary blade, laser cutting, stamp cutting using a blade or a patterned stamping die (e.g., compound or combination die), blade cutting, etc. Sectioning the matrix separates, segments, and/or shapes the continuous matrix into a plurality of individual matrix sections devices, device matrixes, test strips, or other individual device sections. Subsequently, each individual device matrix may be packaged by, for example, placing and sealing each matrix into a pouch such as a moisture proof or waterproof pouch. The pouch can be a foil, plastic film, or a water dispersible and/or water soluble material. In an embodiment, a water dispersible and/or water soluble, biodegradable moisture barrier material may be used for the pouch.

The sealed pouch may packaged to include a desiccant. In an embodiment, the desiccant may be a hot-melt desiccant or other desiccant coating on an inside surface of the packaging or pouch. A non-permanent (removable) desiccant film or laminate cover may be added to each device for protection, which is peeled off or otherwise removed prior to use of the device. Silica gel or other desiccant can be printed directly onto each device to eliminate the need for, or to augment, a secondary desiccant. In embodiment, the sealed pouch may include another chemical stabilizer. For example, the pouch may be nitrogen-purged before sealing to eliminate or otherwise control oxygen and moisture within the pouch. In an embodiment, placement of the matrix and reagent within the pouch and/or sealing of the pouch may be performed in a nitrogen atmosphere.

One or more sealed pouches may be packaged along with instructional materials in an outer package that may include a variety of different forms, including boxes, envelopes, hang-bags, etc. One or both of the instructions and outer package may be manufactured from a variety of water-dispersible and/or water-soluble and/or biodegradable materials such as paper or another cellulosic material.

Manufacturing equipment may be custom manufactured or off the shelf, or a combination thereof. The assembly may be automated through the use of operational software and hardware.

At any point in the device-forming line process, other optional manufacturing stages may be performed to provide the product with one or more functional and/or aesthetic characteristics. These optional manufacturing stages may include calendaring, cutting, perforating, embossing, compression molding or other molding, laser cutting or perforation, additive manufacturing (for example, including the use of 3D printer paper available from, for example, Mcor Technologies of Dunleer, Co. Louth, Ireland), scoring, stamping, folding, rolling, etc. Further, a device formed in accordance with an embodiment can include other structures that are not individually depicted for simplicity. For example, a device may be formed to include an electrical circuit for control or other functions, in which the electrical circuit itself may be wholly or largely water dispersible and/or water soluble after use.

Figure 3A:
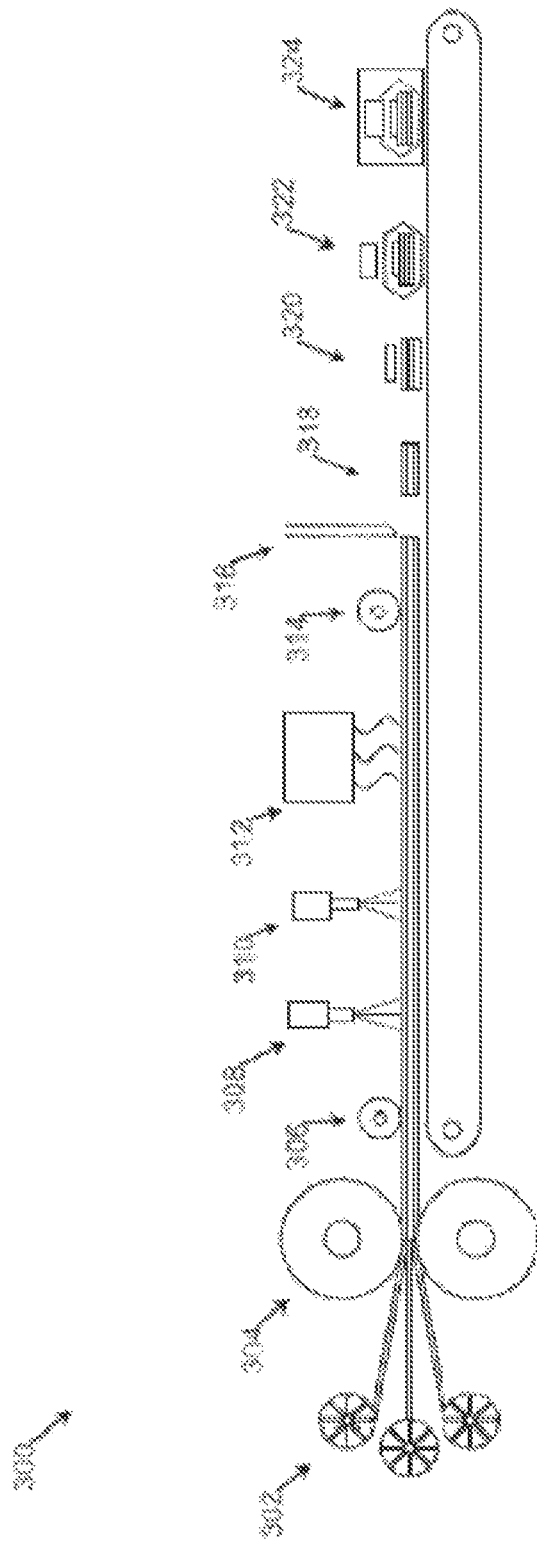
FIG. 3A is a schematic depiction of a continuous manufacturing line and associated equipment for fabricating a test diagnostic device.

FIG. 3A is a cross section depicting a continuous manufacturing process 300 of a testing device in accordance with an embodiment of the present teachings. While FIG. 3A depicts a plurality of separate equipment in a line, it will be appreciated that this manufacturing technique can be in a line or all housed in one machine. At 302, a plurality of matrix layers may be unwound from a plurality of reels and laminated together 304 to form a matrix or web. The matrix may also be a single layer or a plurality of pre-laminated layers unwound from one reel. At 306, one or more channels may be formed in the matrix. At 308, one or more reagents may be applied to the matrix, and at 310 one or more graphics, text, or other indicia may be applied to the matrix. At 312, the reagents and/or indicia may be dried or otherwise cured, for example, using a heated blower, a radiant heat source, or another curing process. At 314, a collection pad 912 (e.g., FIG. 9) may be formed using an embossing process or another process as described herein, for example, with reference to FIG. 9 discussed below. At 316, the matrix may be segmented, shaped, and/or formed into a plurality of individual test strips, test devices, or device subsections. At 320, a desiccant and/or other chemical stabilizer may be added. At 322, the device may be placed into a pouch or other holder and instructions may be added. At 324, one or more pouches and instructions may be packaged in an outer package for shipment to a storage facility, wholesaler, retailer, or end user.

It will be understood that the process 300 of FIG. 3A may be a continuous in-line process performed by one or more machines, or the process may be segmented into two or more batch sub-processes performed by two or more machines. Batch sub-processes may be performed at the same or different manufacturing facilities. In an embodiment, the process 300 may be fully automatic, partially automatic and partially manual, or fully manual. Any one or all of the test device components depicted at 318, the desiccant at 320, the pouch and instructions at 322, and the outer package at 324 may be water-dispersible and/or water-soluble and/or biodegradable, and may be flushable and therefore disposable within a commode. The method 300 of FIG. 3A can include other processing acts or elements that are not depicted for simplicity, while various depicted processing acts or elements 302-324 may be removed or modified.

Figure 3B:
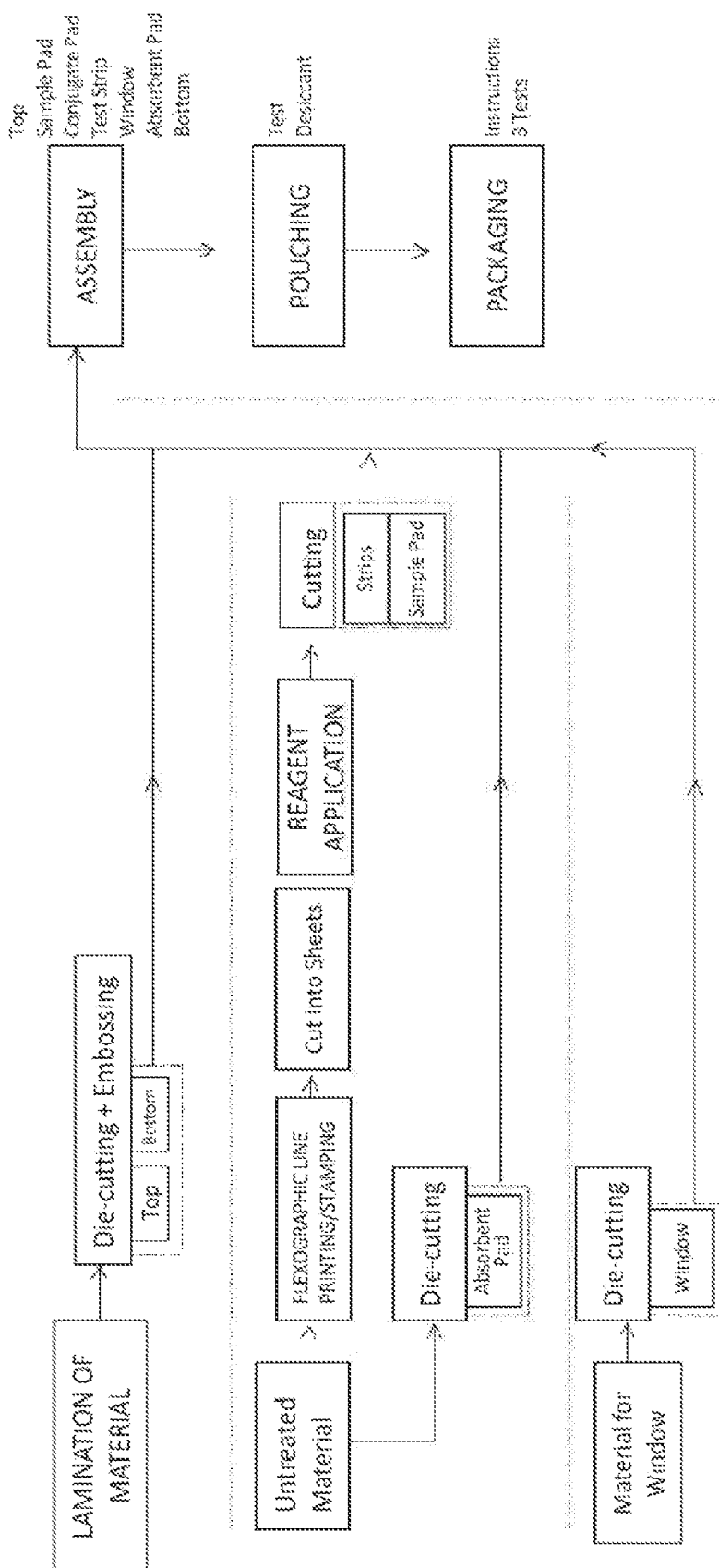
FIG. 3B depicts a process flow chart related to device manufacture.

FIG. 3B provides a process flow chart related to the manufacture of certain exemplary devices contemplated herein.

FIGS. 4-7 depict other embodiments of an immunoassay device used, for example, in diagnostic testing. The devices of FIGS. 4-7 may be formed using an embodiment of the present teachings.

Figure 4A:
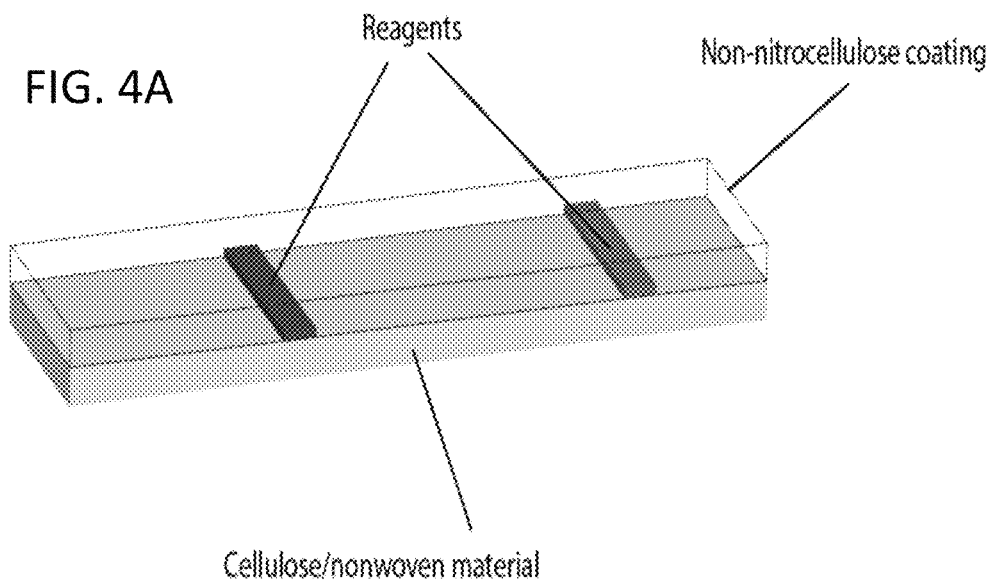
FIG. 4A and FIG. 4B depict certain arrangements of device materials and reagents.

In FIG. 4A, the device includes a non-nitrocellulosic coating over the reagents.

Figure 4B:
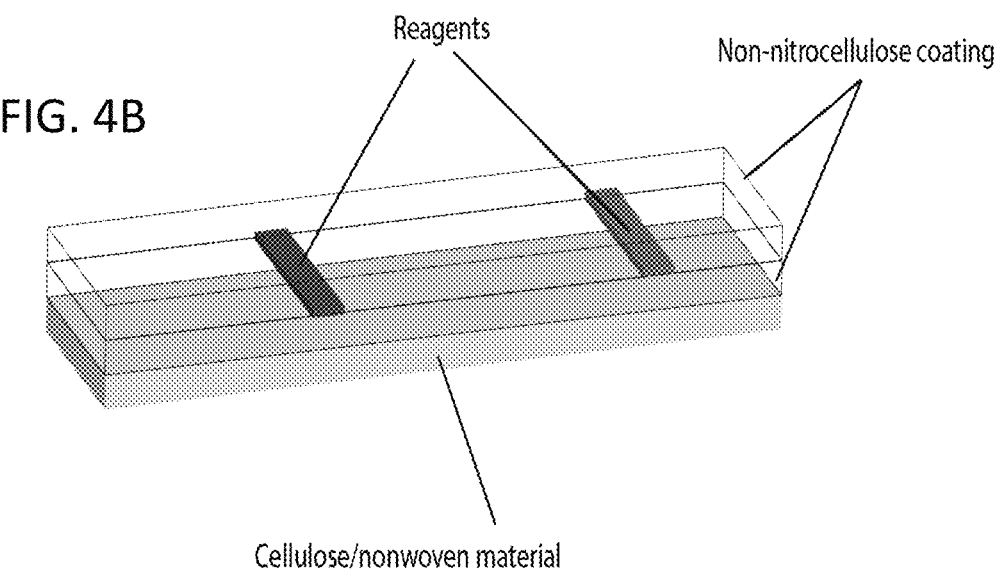

In FIG. 4B, the device includes the reagents sandwiched between non-nitrocellulosic coatings.

Figure 5A:
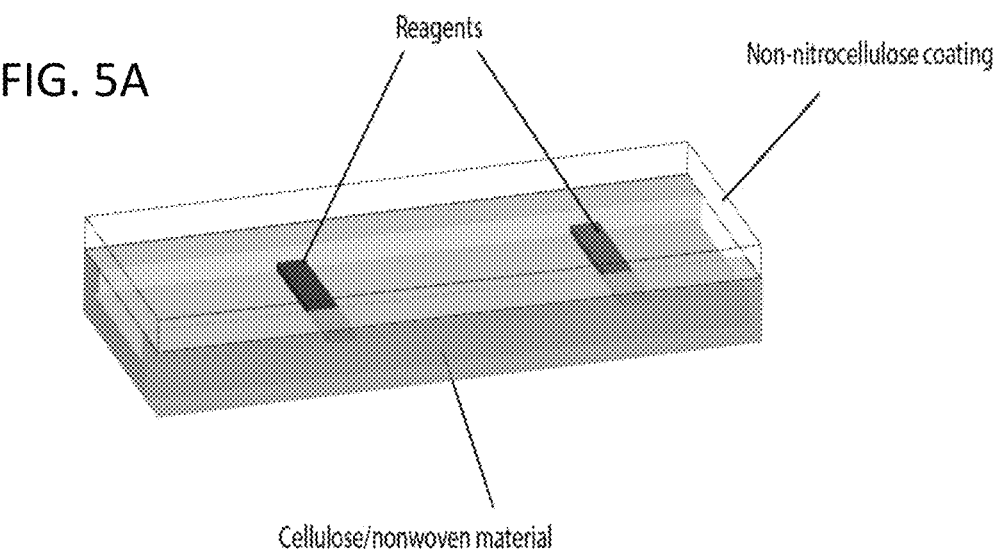
FIG. 5A and FIG. 5B depict certain other arrangements of device materials and reagents.

In FIG. 5A, the device includes a non-nitrocellulosic coating over the reagents, for example, to protect the reagents. The channel may be formed from laminated matrix layers as depicted. The reagents may be exposed at one or both ends to allow biological material to access and physically contact the reagents.

Figure 5B:
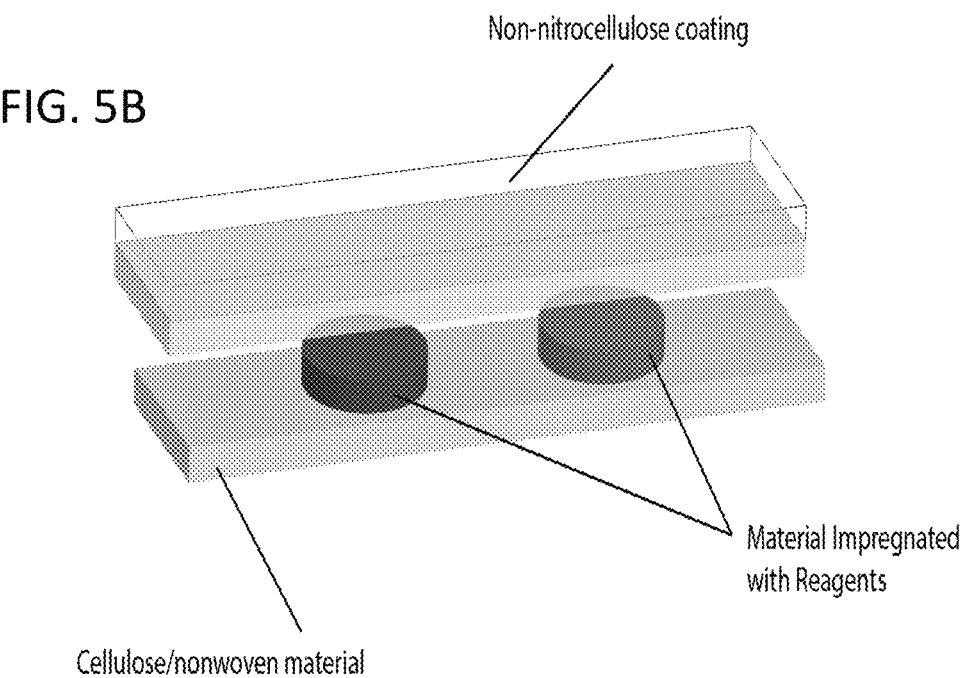

In FIG. 5B, the matrix may be impregnated with one or more reagents. In an embodiment, the reagents may be placed on, over, or within a first matrix layer, then a second matrix may be laminated together such that the reagents are interposed or sandwiched between the first matrix layer and the second matrix layer. The reagent may be embedded or impregnated into another material, such as a cellulosic material or another water-soluble and/or water-dispersible material, and then dispensed over, on, or within the first matrix, then laminated with the second matrix.

Figure 6A:
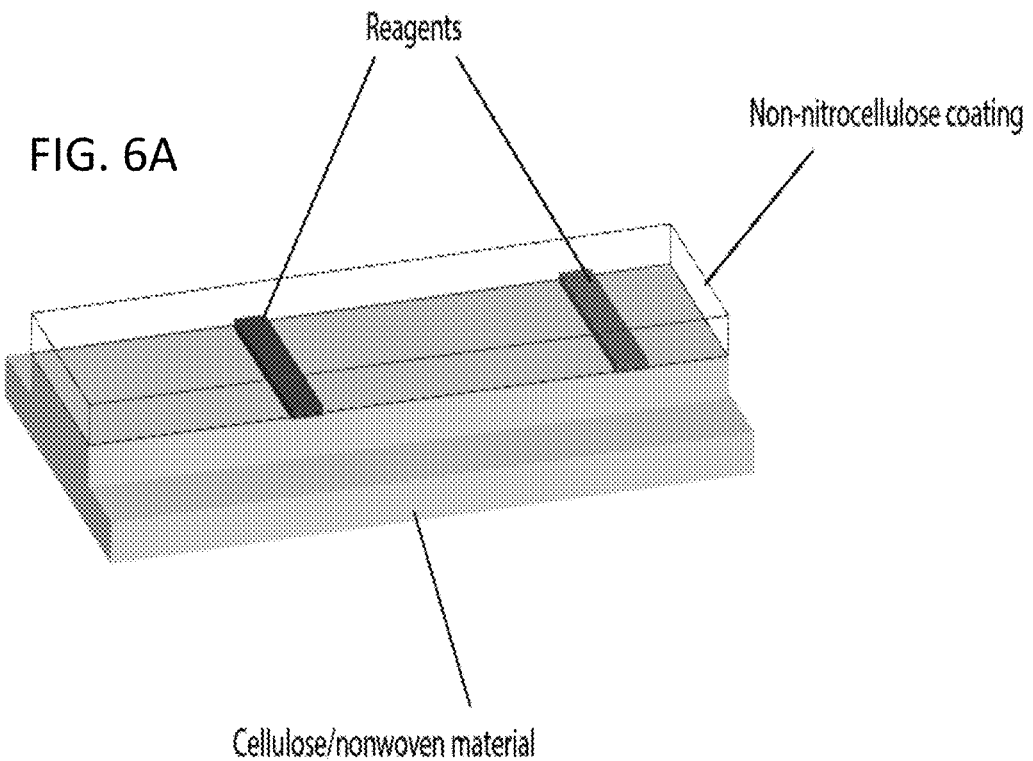
FIG. 6A and FIG. 6B depict certain other arrangements of device materials and coatings.

As depicted in FIG. 6A, the matrix may be patterned, for example, by laminating or layering two or more matrix layers together, or by selective removal of a portion of one or more matrix layers.

Figure 6B:
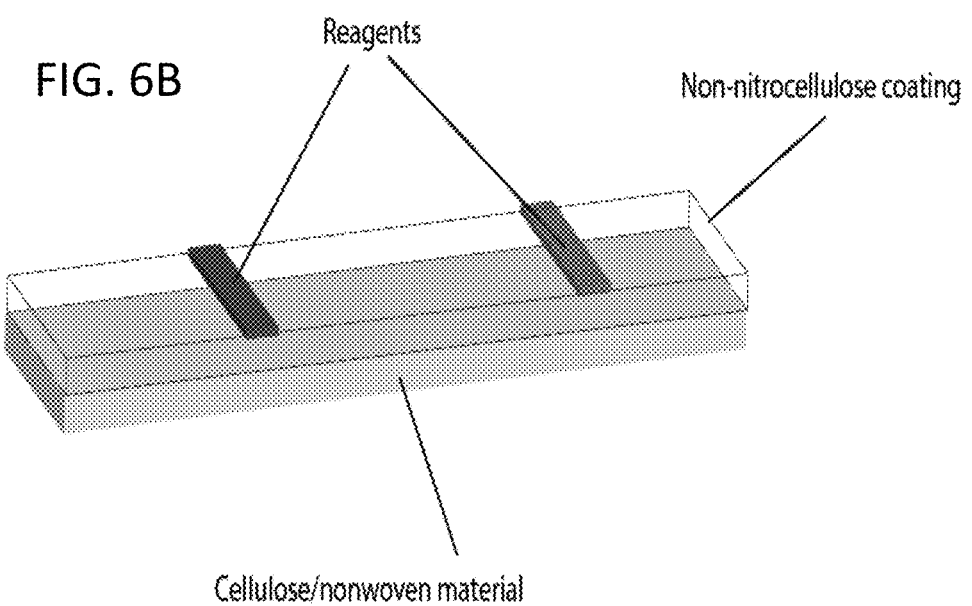

As depicted in FIG. 6B, a non-nitrocellulose coating may be applied or dispensed to the matrix, and one or more reagents may be applied or dispensed onto the non-nitrocellulose coating.

Figure 7:
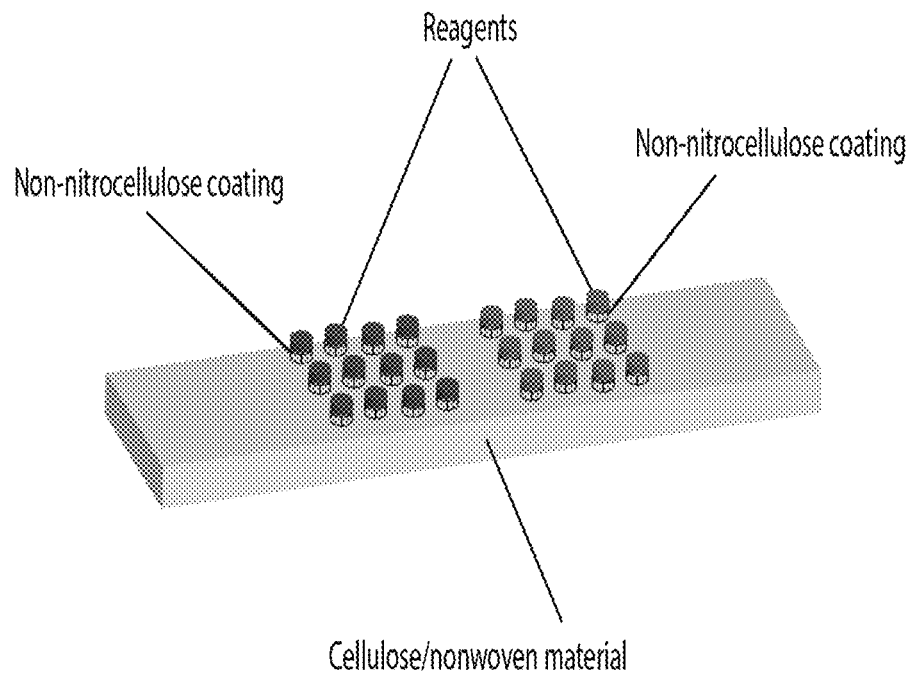
FIG. 7 depicts a dot matrix arrangement of reagent on a matrix material.

As depicted in FIG. 7, a non-nitrocellulose coating and/or one or more reagents may be applied in a pattern on the matrix, such that the reagent is physically separated from the matrix.

Figure 9:
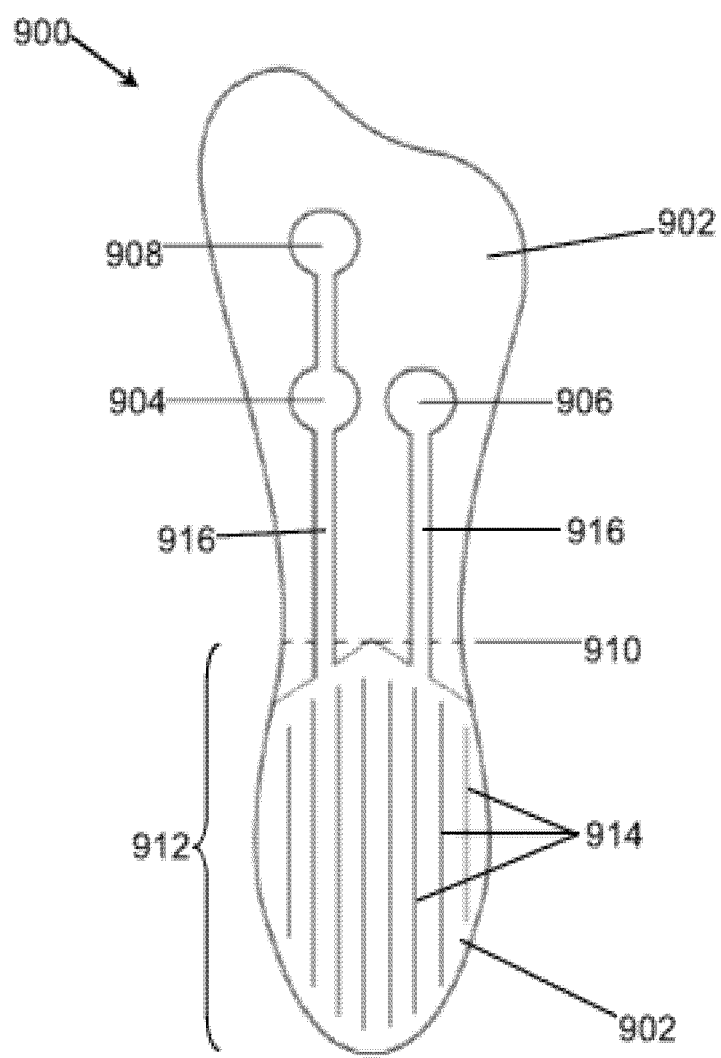
FIG. 9 is a plan view depicting a diagnostic test device formed in accordance with an embodiment of the present teachings.
Figure 10:
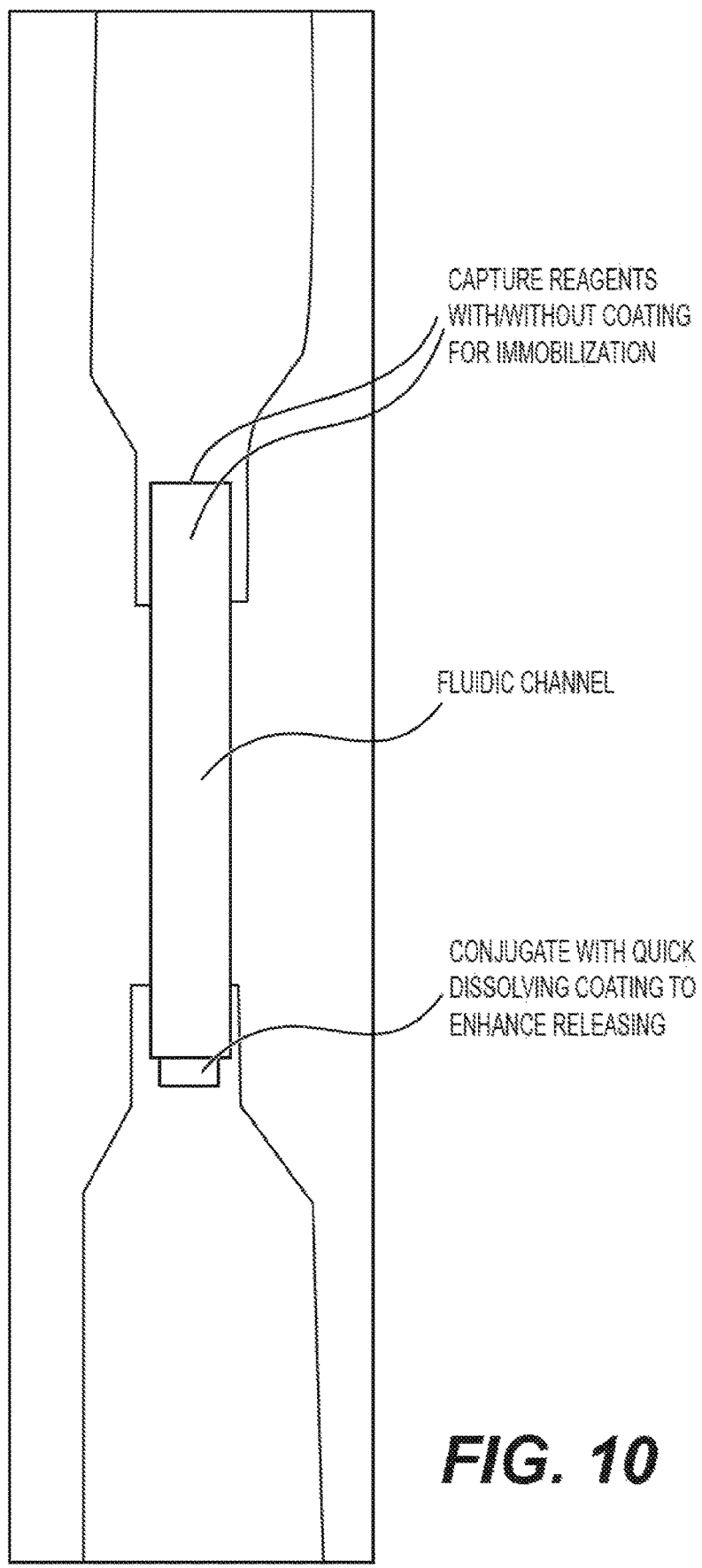
FIG. 10 depicts an embodiment having a single type of, and layered, matrix material as each zone or component of a device.

In an embodiment, the structures of FIGS. 1 and 4-7 may be various embodiments of a test strip used to test for the presence of a chemical. In another embodiment, the structures of FIGS. 1 and 4-7 may depict only a portion of a larger test device, for example, a test device as depicted in FIG. 9. FIG. 9 is a plan depicting an axial device 900 that may be formed in accordance with an embodiment of the present teachings, for example, in a continuous process or in a batch process. The FIG. 9 structure may include a matrix or web 902 as described above, an immunoassay 904 including one or more reagents as described above, a volume indicator 906 for indicating a volume of a collection sample, a control indicator 908, a perforation or tear line 910, a collection pad 912, and one or more channels 914 within which the one or more reagents (FIG. 1) are formed. The arrangement of the various elements of FIG. 9 is not the only one contemplated and should not be limited to this layout or individual elements.

The axial device 900 may be formed in a continuous manufacturing process similar to that depicted at FIG. 3A. In an embodiment, the immunoassay 904, the volume indicator 908, and the control indicator 908 may be formed in one or more channels on or within the matrix 902 as described above. The collection pad 912 may be formed to include a plurality of embossed fluid diversion conduits or channels that, for example, direct fluid flow in a direction toward the one or more reagent channels. The fluid diversion conduits may be formed on or within the matrix using any suitable technique such as embossing the matrix 902 with a wheel or blade, stamping the matrix with a stamp, removing a portion of the matrix using a blade or a laser, or another suitable technique. Embossing the matrix to form the conduits of the collection pad can compact the matrix and increase a density of the matrix material at the embossed conduits, thereby increasing hydrophobicity of the matrix at the conduits to better direct the flow of a fluid test sample toward the reagent channels and toward the reagent. Embossing the matrix can also be used to form a collection pad pattern to increase the matrix surface area, thereby improving absorption of a fluid test sample into the matrix at the embossed collection pad location.

Thus an embodiment of the present teachings may form a diagnostic test device using a continuous manufacturing process or a batch process that is wholly or largely automated. As such, a completed device may have a lower production cost than other devices resulting from conventional diagnostic test device formation processes. The entire test device (matrix or web and reagent) may be water-dispersible and/or water-soluble and/or flushable for easy disposal after use. The packaging materials may be wholly or largely water dispersible and/or water soluble and/or flushable after use.

While the present teachings are described herein with reference to immunoassay and medical testing and diagnostics, the technology described herein may be applied to any lateral flow diagnostics, for example, for use in other industries such as environmental control, food safety, or other industries using axial flow testing technology.

Figure 11:
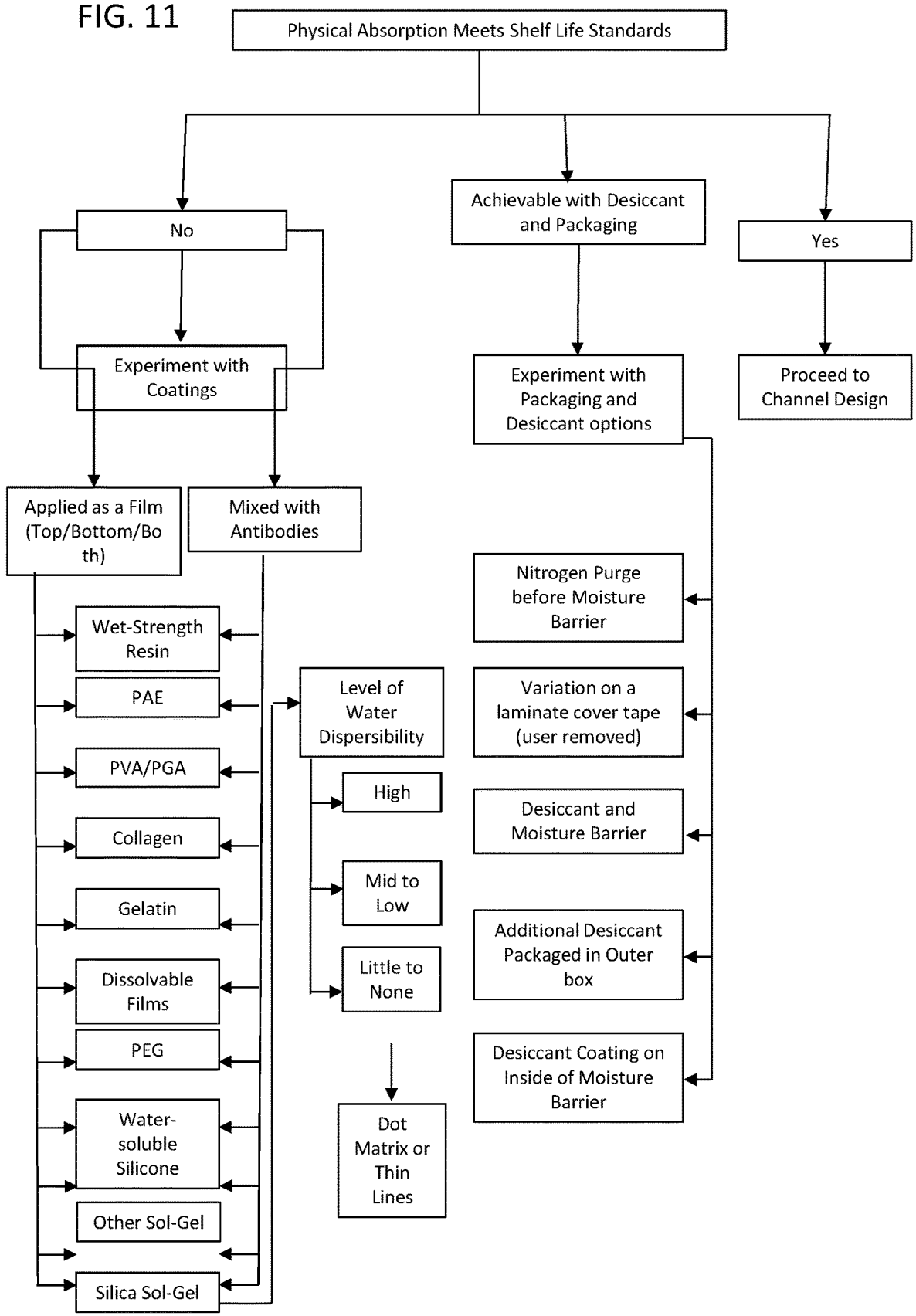
FIG. 11 depicts a process flow chart related to shelf life.

Referring to FIG. 11, a flow chart is presented that provides a high-level of a decision chart related to detection to utilize a coating or special packaging solution in the devices described herein. For example, if the device meets shelf-life standards of sufficient operability at 2 years shelf-life (or another shelf-life standard), a coating or special packaging may not be employed. The center column of the diagram depicts some exemplary options where shelf life extensions are achievable via the use of packaging solutions. An option that is often employed includes using a nitrogen purge of packaging materials prior to enclosing a device in a moisture-tight packaging material. Nitrogen purging creates a low level oxygen or oxygen free environment in the packaging material. Another option includes the use of a cover for the device in the form of a removable film or tape that is removed prior to use of the device. Preferably, the cover is comprised of a water dispersible or water soluble polymer. Another option is often the use of a desiccant material together with the device within a moisture-tight packaging material. Another option is often the inclusion of a desiccant material within a box or container that holds one or more devices that may optionally be individually wrapped. In another frequent embodiment, a nitrogen purge and a desiccant are employed. It is important to appreciate that packaging solutions described herein are not necessarily employed when shelf-life is sub-optimal in a device. Rather, these packaging solutions are often utilized to provide a robust packaging solution such that devices, when shipped, do not require special care or to permit these devices to be stored in any of a variety of environments (including high heat and humidity environments) without affecting the overall efficacy of the devices over a prolonged period of time.

Figure 8:
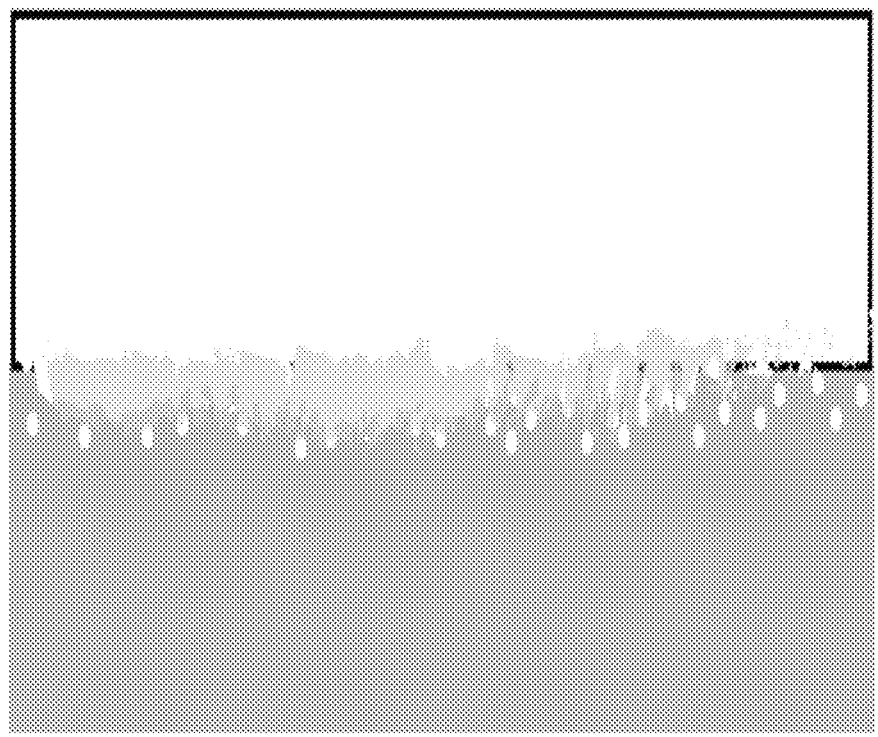
FIG. 8 depicts a profile view of the matrix material of a device, having a coating material and a reagent embedded within and above the matrix material.

Also referring to FIG. 11, the use of coatings is often considered to enhance the shelf-life and robustness of the presently contemplated devices. In particular, reagents such as antibody reagents can be applied to the device and covered with a coating, reagents can be mixed with the coating and applied together to the device, reagents can be positioned on a coating previously applied to the device, or reagents can be positioned on a coating previously applied to the device and below another coating. FIGS. 4-8 depict generic examples of these embodiments, including control and test lines. FIG. 8 shows a coating positioned on a presently contemplated matrix, where the coating is both on top of and partially absorbed or integrated into the matrix. A variety of coating options noted above are also set forth in FIG. 11. Interestingly, the inventors have discovered that certain coatings that work in the presently contemplated assay have low solubility, also referred to as low dispersibility in water. In such circumstances, the coating is often included in a rationed format rather than simply coating the entire device. For example, such coatings (and reagents) are frequently included on devices using a dot matrix style application, positioned in discreet dots. Often the coating and reagent is not contiguous between each discreet dot. Less occasionally, some of the dots, but not all of the dots are interconnected. Thin lines are another option for employing coatings that have low water dispersibility or solubility. Conversely, if the coatings have a low to mid, or a high, dispersibility in water (or target sample fluid) then the coating may be employed in larger amounts or more liberally within predefined regions of the device.

In certain embodiments, shelf-life determinations, predictions and decisions are made using techniques known in the art, for example those detailed in Woo et al., "Shelf-Life Prediction Methods and Applications," Med. Plastics & Biomat. Mag. (March 1996).

Figure 12:
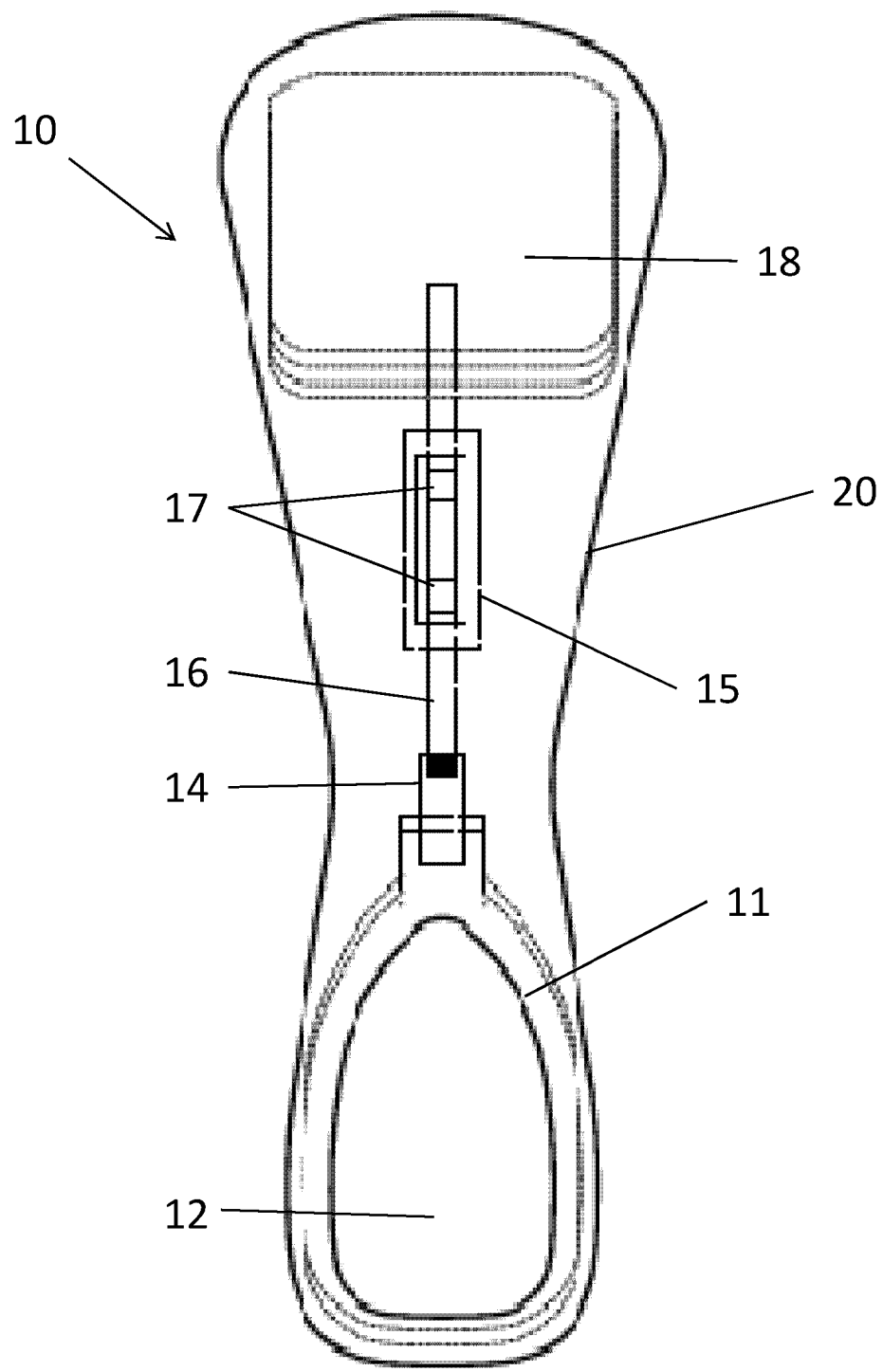
FIG. 12 depicts a line drawing of an exemplary device, including its various aspects.

With reference to FIG. 12, this provides a depiction of various components of an embodiment of an exemplary device (10) as contemplated and described herein. Sample receiving zone (12), label zone/label pad (14), test strip (16), test and control zones (17) in the test region, and absorbent zone (18) are depicted in a support layer (20). An opening or window aligned with the sample receiving zone (11) and test region (15) is provided in the support layer (20) in the depicted embodiment. In frequent embodiments, the label zone/label pad (14) and absorbent zone (18) are covered by or encompassed within the support layer (20). If the support layer (20) is opaque, as is often the case, then portions of the device not exposed via an opening or window would not be visible to a user of the device. Each of the sample receiving zone (12), label pad (14), test strip (16), and absorbent zone (18) are in fluid communication. Multiple layers of sample receiving zone (12) and/or absorbent zone (18) portions are depicted and may optionally be provided. In certain embodiments, 1-10 layers of matrix material (or a matrix material with a larger vertical cross-section) are provided for the sample receiving zone. The windows or openings (11, 15) generally have functional purposes. For example, the opening or window (11) is an area where a sample can be contacted with the sample receiving zone to initiate an assay. Opening or window (15) is an area the test region is viewable, thus this opening or window provides optical communication to the test region (or results therefrom) from outside the device. In certain embodiments, a water dispersible or otherwise dissolvable film (e.g., gelatine) is provided over opening or window (15) in housing/covering layer (20) to protect the test region and optionally enhance readability.

With reference to FIGS. 13A, 13B, and 13C, these provide depictions of various components of an embodiment of an exemplary device (10) as contemplated and described herein. Sample receiving zone (12), test strip (16), test and control zones (17) in the test region, and absorbent zone (18) are depicted in a support layer (20). An opening or window aligned with the sample receiving zone (11) and test region (15) is provided in the support layer (20) in the depicted embodiment. In frequent embodiments, the absorbent zone (18) and portions of the test strip (16) and sample receiving zone (12) are covered by or encompassed within the support layer (20). If the support layer (20) is opaque, as is often the case, then portions of the device not exposed via an opening or window would not be visible to a user of the device. Each of the sample receiving zone (12), test strip (16), and absorbent zone (18) are in fluid communication. The sample receiving zone (12) in this embodiment is comprised of a contiguous matrix material that is folded at portion "R," e.g., to sandwich the test strip (16) between the folded layers. The absorbent zone (18) in this embodiment is comprised of a contiguous matrix material that is folded at portion "R," e.g., to sandwich the test strip (16) between the folded layers. Multiple folded layers of sample receiving zone (12) and/or absorbent zone (18) material may be provided. In certain embodiments, 1-10 layers of matrix material (or a matrix material with a larger vertical cross-section) are provided for the sample receiving zone. The windows or openings (11, 15) generally have functional purposes. For example, the opening or window (11) is an area where a sample can be contacted with the sample receiving zone to initiate an assay. Opening or window (15) is an area the test region is viewable, thus this opening or window provides optical communication to the test region (or results therefrom) from outside the device. In certain embodiments, a water dispersible or otherwise dissolvable film (e.g., gelatine) is provided over opening or window (15) in support layer (20) to protect the test region and optionally enhance readability.

With reference to FIGS. 14A, 14B, and 14C, these provide depictions of various components of an embodiment of an exemplary device (10) as contemplated and described herein. Sample receiving zone (12), test strip (16), test and control zones (17) in the test region, and absorbent zone (18) are depicted in a support layer (20). An opening or window aligned with the sample receiving zone (11) and test region (15) is provided in the support layer (20) in the depicted embodiment. In frequent embodiments, the absorbent zone (18) and portions of the test strip (16) and sample receiving zone (12) are covered by or encompassed within the support layer (20). If the support layer (20) is opaque, as is often the case, then portions of the device not exposed via an opening or window would not be visible to a user of the device. Each of the sample receiving zone (12), test strip (16), and absorbent zone (18) are in fluid communication. In the depicted embodiment, the sample receiving zone (12) and test strip (16) are formed of the same contiguous material, without overlapping contact of different components to provide fluid communication therebetween. The sample receiving zone (12) in this embodiment is comprised of a contiguous matrix material that is folded at portion "R." The absorbent zone (18) in this embodiment is comprised of a contiguous matrix material that is folded at portion "R," e.g., to sandwich the test strip (16) between the folded layers. Multiple folded layers of sample receiving zone (12) and/or absorbent zone (18) material may be provided. In certain embodiments, 1-10 layers of matrix material (or a matrix material with a larger vertical cross-section) are provided for the sample receiving zone. The windows or openings (11, 15) generally have functional purposes. For example, the opening or window (11) is an area where a sample can be contacted with the sample receiving zone to initiate an assay. Opening or window (15) is an area the test region is viewable, thus this opening or window provides optical communication to the test region (or results therefrom) from outside the device. In certain embodiments, a water dispersible or otherwise dissolvable film (e.g., gelatine) is provided over opening or window (15) in support layer (20) to protect the test region and optionally enhance readability.

Figures 15A, 15B:
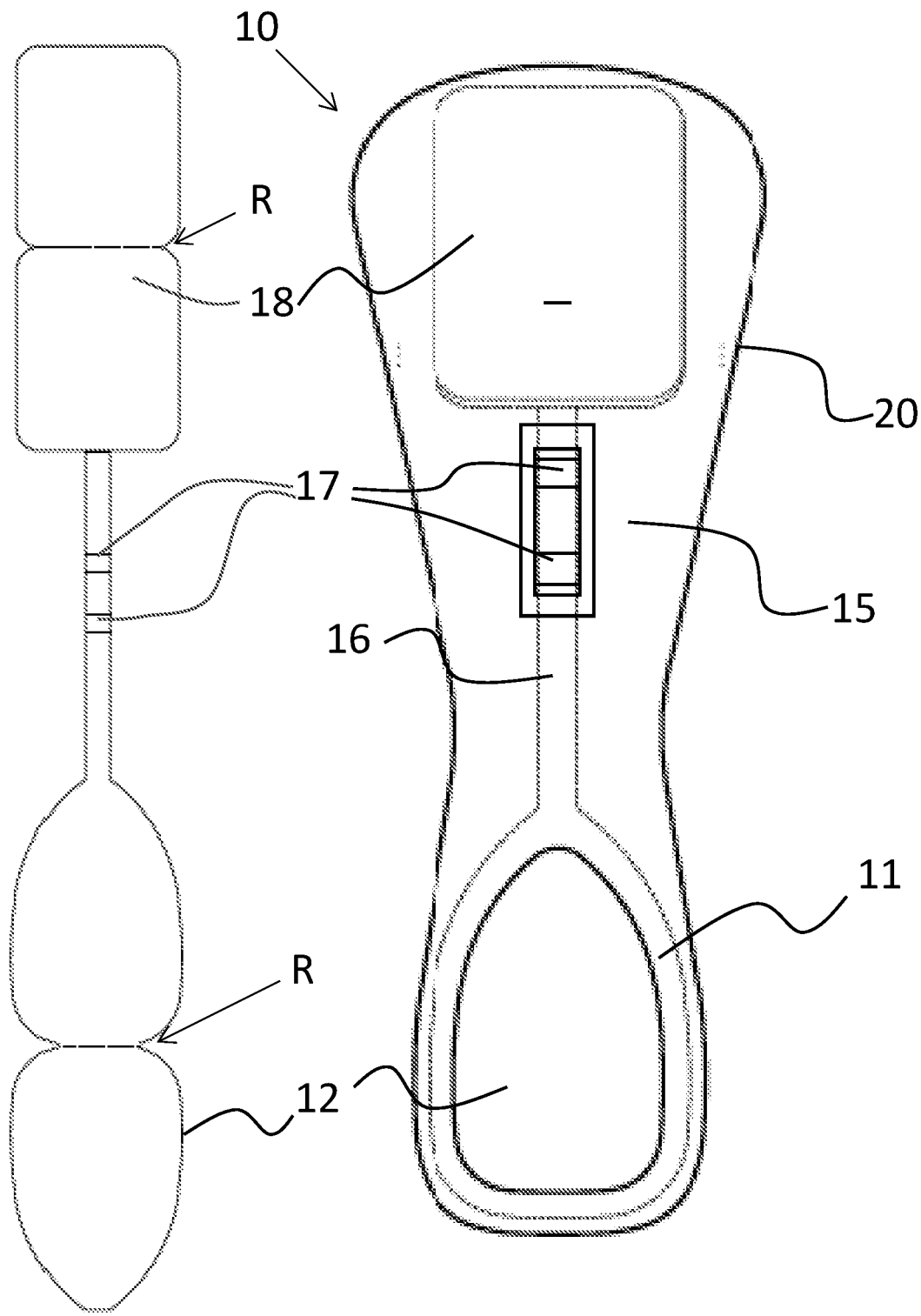
FIG. 15A depicts a line drawing of another exemplary device, including its various aspects.
FIG. 15B depicts a line drawing of an embodiment of a combined sample receiving zone, test strip, and absorbent zone of an exemplary device.

With reference to FIGS. 15A and 15B, these provide depictions of various components of an embodiment of an exemplary device (10) as contemplated and described herein. Sample receiving zone (12), test strip (16), test and control zones (17) in the test region, and absorbent zone (18) are depicted in a support layer (20). An opening or window aligned with the sample receiving zone (11) and test region (15) is provided in the support layer (20) in the depicted embodiment. In frequent embodiments, the absorbent zone (18) and portions of the test strip (16) and sample receiving zone (12) are covered by or encompassed within the support layer (20). If the support layer (20) is opaque, as is often the case, then portions of the device not exposed via an opening or window would not be visible to a user of the device. Each of the sample receiving zone (12), test strip (16), and absorbent zone (18) are in fluid communication. In the depicted embodiment, the sample receiving zone (12), test strip (16), and absorbent zone (18) are formed of the same contiguous material, without overlapping contact of different components to provide fluid communication therebetween. The sample receiving zone (12) in this embodiment is comprised of a contiguous matrix material that is folded at portion "R." Similarly, the absorbent zone (18) in this embodiment is comprised of a contiguous matrix material that is folded at portion "R." Multiple folded layers of sample receiving zone (12) and/or absorbent zone (18) material may be provided. In certain embodiments, 1-10 layers of matrix material (or a matrix material with a larger vertical cross-section) are provided for the sample receiving zone. The windows or openings (11, 15) generally have functional purposes. For example, the opening or window (11) is an area where a sample can be contacted with the sample receiving zone to initiate an assay. Opening or window (15) is an area the test region is viewable, thus this opening or window provides optical communication to the test region (or results therefrom) from outside the device. In certain embodiments, a water dispersible or otherwise dissolvable film (e.g., gelatine) is provided over opening or window (15) in support layer (20) to protect the test region and optionally enhance readability.

With reference to FIGS. 16A and 16B, these provide depictions of various components of an embodiment of an exemplary device (10) as contemplated and described herein. Sample receiving zone (12), test strip (16), test and control zones (17) in the test region, and absorbent zone (18) are depicted in a support layer (20). An opening or window aligned with the sample receiving zone (11) and test region (15) is provided in the support layer (20) in the depicted embodiment. In frequent embodiments, the absorbent zone (18) and portions of the test strip (16) and sample receiving zone (12) are covered by or encompassed within the support layer (20). If the support layer (20) is opaque, as is often the case, then portions of the device not exposed via an opening or window would not be visible to a user of the device. Each of the sample receiving zone (12), test strip (16), and absorbent zone (18) are in fluid communication. In the depicted embodiment, the sample receiving zone (12), test strip (16), and absorbent zone (18) are formed of the same contiguous material, without overlapping contact of different components to provide fluid communication therebetween. Multiple layers of sample receiving zone (12) and/or absorbent zone (18) material may be provided. In certain embodiments, 1-10 layers of matrix material (or a matrix material with a larger vertical cross-section) are provided for the sample receiving zone. The windows or openings (11, 15) generally have functional purposes. For example, the opening or window (11) is an area where a sample can be contacted with the sample receiving zone to initiate an assay. Opening or window (15) is an area the test region is viewable, thus this opening or window provides optical communication to the test region (or results therefrom) from outside the device. In certain embodiments, a water dispersible or otherwise dissolvable film (e.g., gelatine) is provided over opening or window (15) in support layer (20) to protect the test region and optionally enhance readability.

Figure 17A:
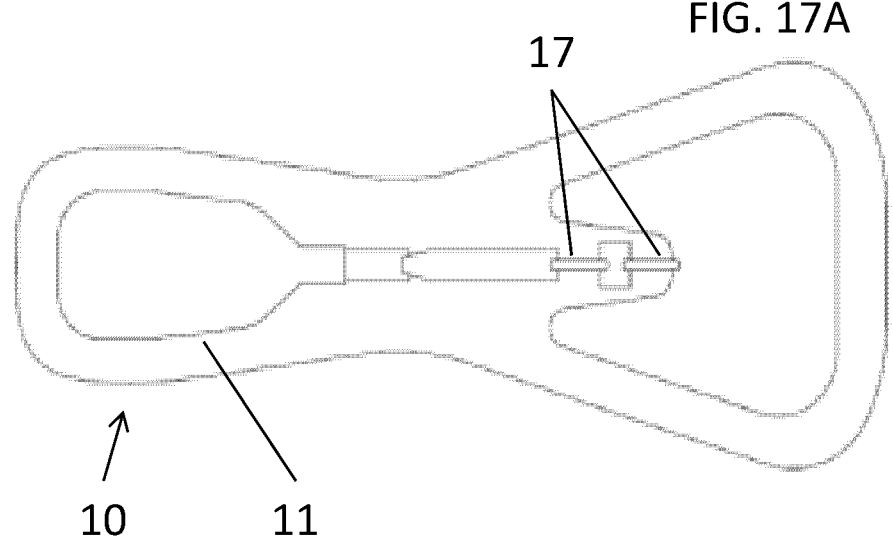
FIG. 17A depicts a line drawing of another exemplary device, including its various aspects.
Figure 17B:
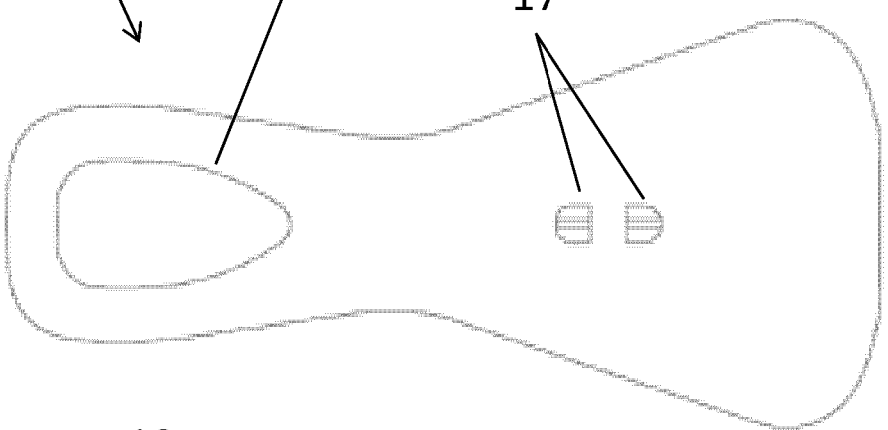
FIG. 17B depicts a line drawing of the device of FIG. 17A, including the top portion of the housing.
Figure 17C:
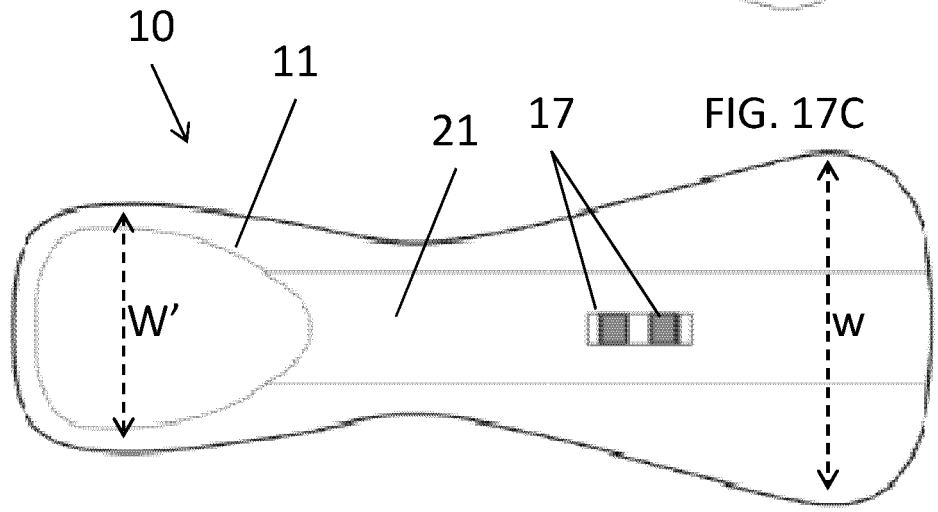
FIG. 17C depicts a line drawing of another exemplary device, including its various aspects.

With reference to FIGS. 17A, 17B, and 17C, these provide depictions of various exemplary devices (10) as contemplated and described herein. While not labeled, similar aspects of these devices can be determined with reference to, for example, FIGS. 12-16. The absorbent zone of FIG. 17A is depicted as wrapping around the test strip portion, which represents one exemplary arrangement of the absorbent zone for any embodiment described herein. Since the matrix material is often an absorbent-type material, a physical orientation of an absorbent material that is spread in horizontal or vertical directions about or relative to the test strip often assists absorption or wicking of sample into the absorbent zone that has passed through the test zone. As also can be seen in FIG. 17A (in addition to other Figures provided herein), the sample zone may be configured to provide a narrowed portion leading to the test strip to confine or focus or liquid flow in the matrix material from the sample zone to the test strip or test zone. With further regard to FIG. 17A, the test zone may include narrow portions of matrix material for the test and/or control zones, which often aid in providing a highly visually distinguishable result (test or control line visibility).

With regard to FIG. 17C, aspects W and W' are highlighted using a dotted arrow. These portions refer to the width of the device (and other exemplary devices described herein), which in frequent embodiments is often selected to be narrower than the trap on a standard toilet. Vent/raised portion (21) is also depicted in this embodiment, which provides for venting and/or accommodating a test strip within the support. While not depicted in other embodiments, raised portion (21) may be provided in other embodiments described herein. With further reference to aspects W and W', either or both of these aspects most frequently measure less than 3". In certain embodiments, W and W' measure between about 2" to about 4", or about 2", 2.10", 2.17", 2.20, 2.3", 2.4", 2.5", 2.6", 2.7", 2.8", or 2.9". Perpendicular to aspects W and W', the length of the device (support included) may vary. Exemplary lengths of the device may range, for example, between 4" to 12". In certain embodiments, the length of the device is between 5" and 7". In certain embodiments, the length of the device is about 6" or about 6.14".

Figure 18:
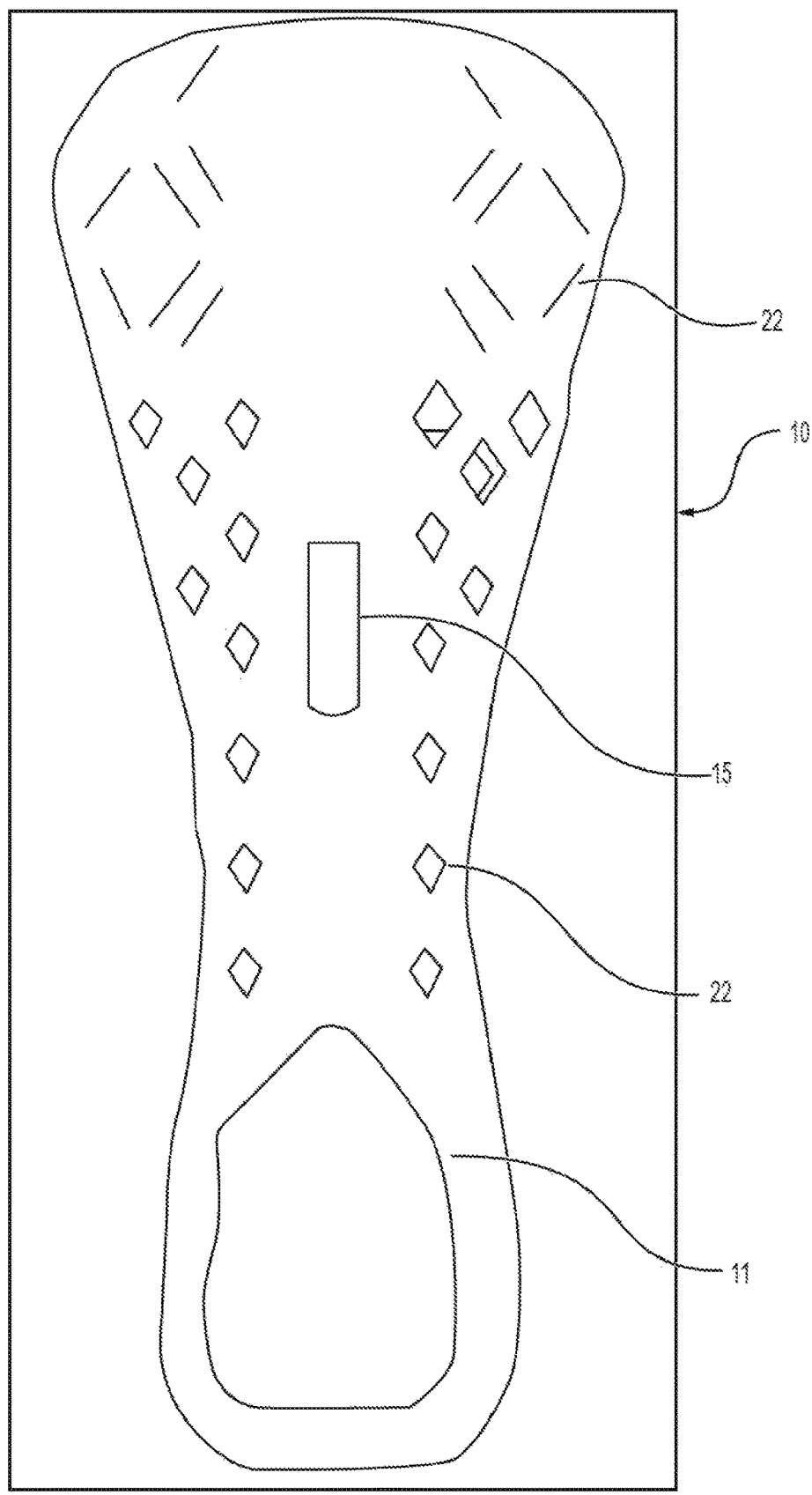
FIG. 18 depicts a line drawing of another exemplary device, including its various aspects.

With reference to FIG. 18, this provides a picture of another exemplary device (10) as contemplated and described herein. While not labeled, similar aspects of these devices can be determined with reference to, for example, FIGS. 12-17. The device depicted in FIG. 18 additionally incorporates cut outs and slits (22) in the support, which enhance the ability of the device to sink and/or be readily flushable. Though not wishing to be bound by any particular theory, cut outs and slits (22) both provide greater access to the internal matrix structure by a liquid, and reduce liquid surface tensions when the device is contacted with a body of liquid, such as the water in a toilet. Such cut outs and slits (22) may be incorporated in the variety of devices contemplated herein to aid in the disposal and flushability of these devices.

Figure 19A:
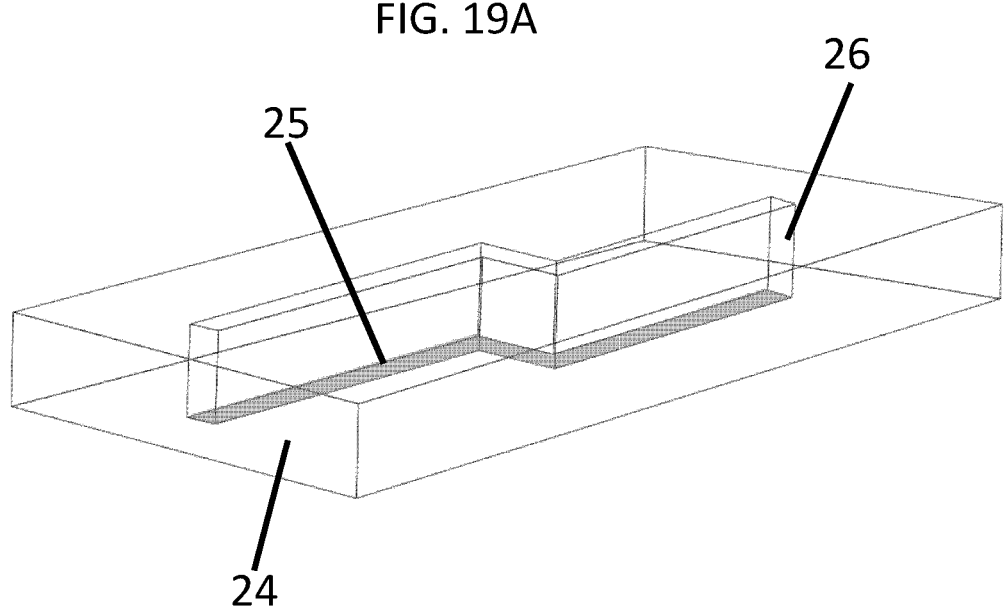
FIG. 19A depicts a line drawing of an embodiment of a portion of an exemplary device, including its various aspects.
Figure 19B:
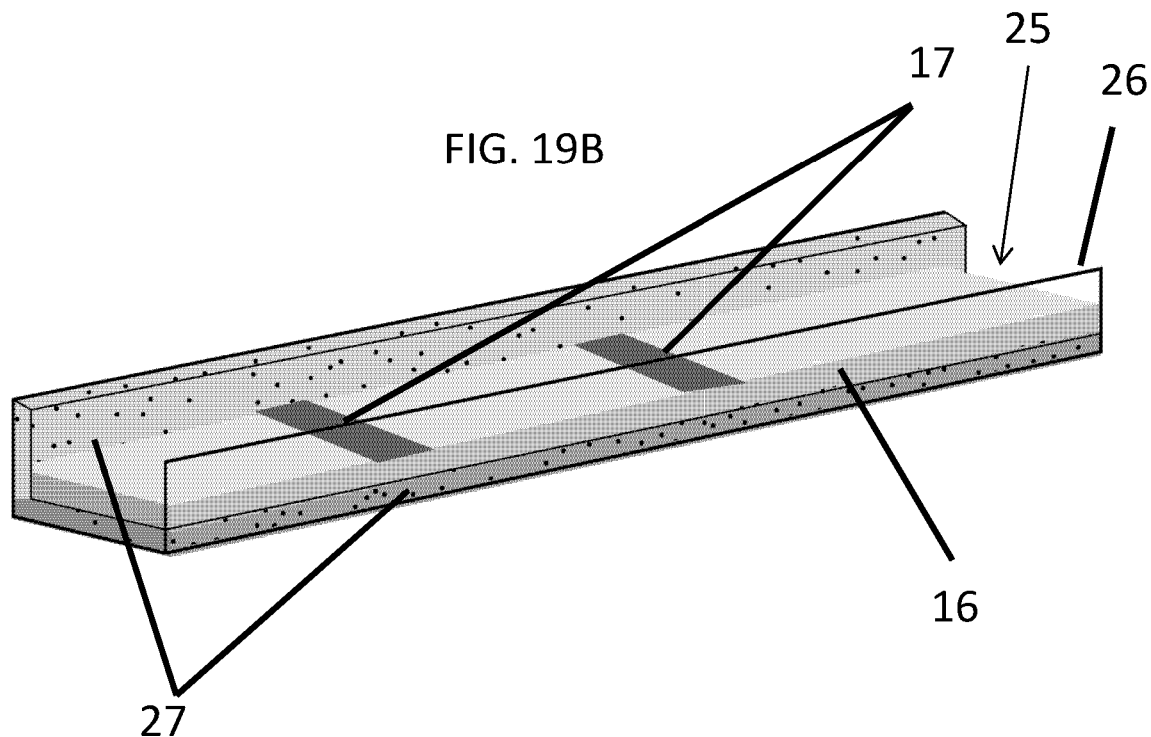
FIG. 19B depicts a magnified portion of the device of FIG. 19A.

With reference to FIGS. 19A and 19B, these provide an embodiment of the present devices that utilize a non-woven support comprising, for example, gelatin or collagen. This embodiment may also be provided or referred to as a water-dispersible microfluidic chip. A diagnostic channel (25) is provided in a gelatin or collagen support (24), formed by a gelatin or collagen wall (26) that may optionally be hydrophobically treated, or lined with a matrix material that is optionally hydrophobically treated (27). The exemplary diagnostic channel (25) includes a non-woven test strip, including test and control zones (17). Such hydrophobic treatment is often only a temporary hydrophobic treatment as contemplated herein, such that moisture or a liquid will eventually permeate into the material for dissolution or dispersal. The non-woven support may be utilized as the support alone, or together with other components such as support materials comprised of matrix material as described herein. The diagnostic channel, though depicted to have a curve, is merely exemplary regarding the multiple configurations of such channels that are contemplated. The diagnostic channel may be a microfluidic channel containing a matrix material contemplated herein. The diagnostic channel will generally be provided in fluid communication with a sample zone (not depicted) and/or an absorbent zone (not depicted). In an exemplary manufacturing process, gelatine may be poured in a mold. Hydrophobic treated matrix material such as HYDRASPUN® is then pressed or placed into mold cavities. The test strip is then placed on the hydrophobic treated matrix material. The diagnostic channel is then optionally covered with additional layer of gelatine that optionally has an opening for a sample entry point. Edges or perimeter is then optionally sealed with a water-soluable pressure sensitive adhesive.

With regard to hydrophobic barriers options contemplated herein, the matrix material may in certain embodiments be laminated with cold-water MonoSol or hot-water MonoSol. The matrix material may also in certain embodiments be treated with a high concentration of starch to enhance rigidity and temporary liquid resilience. The matrix material may also in certain embodiments be coated with ProGel (typical coloration or the white variety treated with titanium dioxide) and an additional barrier may be provided, for example under the sample zone using Soy Wax. The matrix material may also in certain embodiments be treated using Starch+Deionized Water+hydrophobic solution (e.g., DRY- WIRED® Textile Shield; Drywired, LLC). The matrix may also in certain embodiments be treated using Starch+Deionized Water+Silicon Dioxide. The matrix may also in certain embodiments be treated using Starch+hydrophobic solution (e.g., DRYWIRED® Textile Shield). The matrix may also in certain embodiments be treated using another hydrophobic nanoparticle solution.

The issue of meeting flushability guidelines for the present devices is addressed herein. Commercially available materials have been found to be not particularly conducive to meeting these guidelines as a number of problems were encountered and overcome. For example, as indicated, using a lamination process to combine multiple layers of matrix material in ensuring the water-dispersion of the device, where thicker materials would not break apart as readily. The use of embossing or including cutouts and/or slits adapts the surface area and surface tension of the device in liquid. Reducing the width of the shoulders has enhanced flushability, in addition to reducing the amount of material in, and size of, the device. Adjusting the hydrophobic solution to permit liquid absorption at a predetermined time, adding a weighted element to the device, and including a Gelatine window in the device may also be employed.

The presently described devices have overcome a variety of assay performance challenges using innovations described herein. For example, as discussed, antibody reagents are often striped on the matrix material in a direction that is perpendicular to the machine/waterjet direction of the nonwoven matrix material. In frequent embodiments, a separate or distinct label pad is not utilized. Rather, conjugate reagents are provided or striped into the sample zone. This is often performed in alignment with the machine/waterjet direction after the sample zone is treated with buffers and dried. Latex beads are often included to enhance the test signal. Obtaining strongly adhered test and/or control lines on the presently contemplated matrix materials may also be obtained by using pH treatment (e.g., low pH shock) of the antibodies. In certain embodiments, reagent striping is provided on a matrix material that has been treated with a hydrophobic solution such as HYDRASPUN®. The test strip may also be employed in a narrow configuration, which is the opposite versus conventional assays (e.g., 3 mm vs. 5 mm), to enhance (e.g., lower) the time period for results. Considering the nonwoven materials contemplated herein, such narrowing has been shown to provide an improved effect.

Portions of the description stated above may allow for the following non-inclusive improvements of current lateral flow and flow-through device components, including housings therefor. Certain drawings depict merely exemplary configurations and possible applications that utilize coatings and surface treatments to create temporary hydrophobic barriers for stability and/or in place of traditional lateral flow and flow-through assay methods. Material treatments and coatings can be applied in solid (film), liquid, or gel form through a variety of techniques, including non-contact, pump-driven solenoid dispensers; contact tip dispensers, ink-jet printing, spray coating and roll-to-roll applications. This treatment or coating can be used in one, many, or a combination of, ways, such as:
- A final (top) coating, entrapment, acts as a sealant
- A preliminary (base) coating before application of analytes
- Both a preliminary and final coating
- A mixture (mixed with analyte) and placed down
- A treatment of the material substrate/matrix, itself The method for creation of a water dispersible or soluble lateral flow or flow-through device may include some, all or any combination of the following:
- Use of water dispersible or soluble matrices/substrates such as nonwoven cellulose
- Combine some/all components
- Disperse in water
- Aid in sample flow/improve wicking speed
- Coatings or treatments to improve various aspects of assay performance or to control/adjust hydrophobicity of the materials, such as:
- Reagent immobilization
- Bioactivity and shelf life
    - Ex. Laminate cover substitute
- Conjugate release
- Surface modification
    - Ex. Smoother surface
    - Ex. Aid in sample flow
- Creation of channel walls or barriers
- Desiccant
- Surface treatment or lamination for hydrophobicity
- Sample collection/modification
    - Ex. PH adjustment
- Conjugate modification by change in size or use of alternative materials
- Improve readout clarity
- Improve sensitivity/specificity
- Cost efficiency
- Allow for full water-dispersibility Other assay treatments or reagents are also occasionally used, such as:
- Sucrose solutions
- Trehalose Solutions (e.g., Yetisen et al., Lab on a Chip 12 (2013): 2210-2251, 2240)
- LB Medium and Sucrose Coating stabilizer
- Blocking Buffer and Coating Stabilizer
- Acid treatment
- Latex particles
- Cellulose nanobeads
- A coating is also often chosen to provide for a predetermined dissolution rate based on the matrix material of the analyte of interest.

Coatings and treatments are also often formulated for specific performance characteristics, such as dissolution rate, viscosity, layer thickness, and porosity, based on desired application. For example, a coating is often chosen based on its bonding with, adherence to, or integration within, the matrix material. A coating is also often chosen to provide for a predetermined dissolution rate based on the analyte of interest, user type, analyte identification sensitivity desired, among other reasons.

Certain advantages are provided with the currently described materials, methods, and devices. In particular, the device (i.e., assay/test strip/testing device) is dispersible or soluble in water. Most frequently, the device is biodegrade. Fewer components and fewer materials are needed to manufacture and functionally utilize the device according to any desired assay, which permits component integration and eases manufacturing complexities. Materials contemplated herein also provide an option for a quicker assay than is currently available. Multiplexing and or quantitative testing may now be more easily enabled using the devices contemplated herein. In particular, the presently described devices provide for the design and implementation of multiple flow paths or channels on a single device. As such, the same sample can be tested concurrently for the presence of multiple analytes. For example, each of the multiple channels can be adapted to test for a specific hCG level, which can differ between channels. Also, since larger than typical lateral flow devices are provided, the additional space provided on the device can provide for evaluating multiple hCG levels in a single channel or multiple different analytes in a single or different channels. In certain embodiments, the device is provided with multiple channels, where two or more of the channels are provided to evaluate the same analyte (e.g., hCG) in the same level.

The present disclosure provides a test device, particularly immunoassay devices, for determining the presence or absence of multiple analytes in a fluid sample. In general, a test device of the present disclosure includes a matrix defining a flow path. Typically, the matrix further includes a sample receiving zone, a label zone, a test zone and a control zone. In frequent embodiments, a test region comprises the test and control zones. In a related embodiment, the matrix further includes an absorbent zone disposed downstream of the test region. Moreover, in preferred embodiments, the test region, which comprises the test and control zones, is observable. In frequent embodiments, one or more of these zones is/are comprised of a water dispersible or soluble matrix. In the most frequent embodiments, two or more of these zones is/are comprised of a water dispersible or soluble matrix. Often, the entire device is comprised of a water dispersible or soluble matrix, that is frequently a contiguous water dispersible or soluble matrix. In certain frequent embodiments the label zone comprises an insert provided in an assay flowpath comprised in a water dispersible or soluble matrix.

WDMSM was chosen as a material to investigate for the development of an exemplary device. An hCG reagent test kit from Kestrel Biosciences was obtained to investigate the antibody binding properties of WDMSM. Spot testing of antibodies was performed to assess antibodies coating the fibers of the WDMSM material. Lateral flow testing was then performed to assess gold conjugate (liquid conjugate) reagent flow through the WDMSM material and positive results in capture antibody zones. Initial drying down of gold conjugate to the material was performed to evaluate WDMSM as the conjugate pad section of the lateral flow device.

Spot testing showed strong positive results for the Kestrel kit control. Goat anti-Mouse capture antibody was dried down onto WDMSM material. The gold conjugate was then introduced to determine if the capture antibody was attached to WDMSM and was able to detect the Mouse antibody conjugated to the gold particles. These tests showed that antibodies do uniformly attach to WDMSM when they are dried down and the antibodies remain functional. Lateral flow testing was performed with the Kestrel Kit control on WDMSM. These tests showed that the gold conjugate was able to flow through the WDMSM. Also, the capture antibody was able to attach to the gold particles as the gold particles flowed past the capture antibody zone. Lateral flow testing was then performed with the Kestrel Kit control using WDMSM where capture antibody was concentrated in a small area of material. These tests showed that the gold conjugate was able to flow through contiguous and connected sections of WDMSM. Also, the capture antibody was able to attach to the gold particles as the gold particles flowed past the capture antibody zone. The tests showed positive results.

Lateral flow testing with Kestrel's hCG assay and Kit control. Goat anti-hCG capture antibodies were dried down onto small pieces of WDMSM and the test was positive. Goat anti-Mouse capture antibodies were dried down onto small pieces of WDMSM and the test was also positive. The capture antibody coated pieces of WDMSM were attached in sequence with larger WDMSM pieces which acted as a sample receiving zone and absorbent zone to simulate a traditional layout of a lateral flow device. Samples which included the hCG positive control showed that the hCG capture antibody zone turned positive. This shows that the antibodies are functional.

The performance of dried down (on WDMSM) antibodies was then tested using the following compositions or formulations:

Gold conjugate (Kestrel, OD10, 6 ug/ml, lot 033115) mixed with 5% Sucrose and 5% Trehalose 5% Sucrose and 5% Trehalose solution, followed by the addition of gold conjugate (Kestrel, OD10, 6 ug/ml, lot 033115)

Gold conjugate (Kestrel, OD10, 6 ug/ml, lot 033115) followed by the addition of 5% Sucrose and 5% Trehalose solution Gold conjugate (Kestrel, OD10, 6 ug/ml, lot 033115) mixed with 10% sucrose 10% sucrose followed by the addition of gold conjugate (Kestrel, OD10, 6 ug/ml, lot 033115)

Gold conjugate (Kestrel, OD10, 6 ug/ml, lot 033115) followed by the addition of 10% Sucrose Gold conjugate (Kestrel, OD10, 6 ug/ml, lot 033115) mixed with 20% sucrose 20% sucrose followed by the addition of gold conjugate (Kestrel, OD10, 6 ug/ml, lot 033115)

Gold conjugate (Kestrel, OD10, 6 ug/ml, lot 033115) followed by the addition of 20% Sucrose Each of the reagents was dried to a test device comprised of WDMSM prior to further testing. Water was added to the device to mobilize the reagents.

It was found that more gold conjugate with 20% sucrose is released into the test device than gold conjugate with 10% sucrose or with 5% sucrose and 5% trehalose. It was also found that at least some of the antibodies in the gold conjugate retain their shape and functionality after being dried down with 20% sucrose. The goat anti mouse antibody was able to detect the mouse antibodies conjugated to the gold particles in the 20% sucrose dried down gold conjugate. The negative control sample did not capture any released gold conjugate. WDMSM alone is not capturing released gold conjugate. The color change in the coated WDMSM shows that the goat anti mouse antibodies are binding to WDMSM and capturing gold conjugate as it flows through the device. This experiment shows, for example, functionality of the gold conjugate dried with sugar. Latex beans or cellulose nanobeads could be incorporated in lieu of or in addition to gold label material.

The above examples are included for illustrative purposes only and are not intended to limit the scope of the disclosure. Many variations to those methods, systems, and devices described above are possible. Since modifications and variations to the examples described above will be apparent to those of skill in this art, it is intended that this invention be limited only by the scope of the appended claims.

One skilled in the art will appreciate further features and advantages of the presently disclosed methods, systems and devices based on the above-described embodiments. Accordingly, the presently disclosed methods, systems and devices are not to be limited by what has been particularly shown and described, except as indicated by the appended claims. All publications and references cited herein are expressly incorporated herein by reference in their entirety.

We claim:

1. A method for preparing a diagnostic device containing a water dispersible label zone for an immunoassay, comprising ink-jet, flexographic or screen printing a labeled reagent and a water soluble coating agent on a test strip comprised of water dispersible matrix material, treating a support comprised of water-dispersible matrix material with a hydrophobic coating, and positioning the test strip within the support.

2. The method of claim 1, wherein the water dispersible matrix material of the test strip and of the support comprises a water dispersible matrix sandwich material (WDMSM).

3. The method of claim 2, wherein the water dispersible matrix material of the label zone is positioned in contiguous non-overlapping fluid communication with the water dispersible matrix material of the test strip.

* * * * *